(12) United States Patent
Valente et al.

(10) Patent No.: US 7,582,606 B2
(45) Date of Patent: Sep. 1, 2009

(54) NADPH OXIDASE CYTOSOLIC COFACTOR MUTANT

(75) Inventors: Anthony J. Valente, San Antonio, TX (US); Robert A. Clark, San Antonio, TX (US)

(73) Assignee: The Board of Regents of the University Of Texas System, San Antonio, TX (US)

( * ) Notice: Subject to any disclaimer, the term of this patent is extended or adjusted under 35 U.S.C. 154(b) by 0 days.

(21) Appl. No.: 11/556,314

(22) Filed: Nov. 3, 2006

(65) Prior Publication Data

US 2007/0098706 A1 May 3, 2007

Related U.S. Application Data

(60) Provisional application No. 60/733,101, filed on Nov. 3, 2005.

(51) Int. Cl.
*A61K 38/00* (2006.01)
*C07K 14/00* (2006.01)

(52) U.S. Cl. ........................................ 514/12; 530/350

(58) Field of Classification Search .................. None
See application file for complete search history.

(56) References Cited

FOREIGN PATENT DOCUMENTS

EP 1661912 A1 * 5/2005

* cited by examiner

*Primary Examiner*—Anand U Desai
(74) *Attorney, Agent, or Firm*—Gifford, Krass, Sprinkle, Anderson & Citkowski, P.C.

(57) ABSTRACT

A purified polypeptide includes an NADPH oxidase cytosolic cofactor polypeptide NOXA1 or p67$^{phox}$ having a C-terminal SH3 domain insertion mutation of at least three consecutive amino acids positioned between PEDL (SEQ ID NO: 35) and GIFPK (SEQ ID NO: 34) motifs of said SH3 domain so as to reduce activity of the purified polypeptide relative to the wild-type cofactor polypeptide. A process for treating, inhibiting, or prophylactically preventing a disease associated with the overproduction of reactive oxygen species involving NOXn where n is 1-4 inclusive includes the administration of a therapeutically effective amount with a purified polypeptide to a subject tissue that is overproducing reactive oxygen species through a NOXn pathway.

11 Claims, 12 Drawing Sheets

Figure 1

```
             1                                                           60
             |                                                           |
NOXA1        MASLGDLVRAWHLGAQAVDRGDWARALHLFSGVPAPPARLCFNAGCVHLLAGDPEAALRA
NOXA1inhib   MASLGDLVRAWHLGAQAVDRGDWARALHLFSGVPAPPARLCFNAGCVHLLAGDPETALRA
NOXA1trunc   MASLGDLVRAWHLGAQAVDRGDWARALHLFSGVPAPPARLCFNAGCVHLLTGDPEAALRA
             ............................................................
                                       Exon 1
             61                                                          120
             |                                                           |
NOXA1        FDQAVTKDTCMAVGFFQRGVANFQLARFQEALSDFWLALEQLRGHAAIDYTQLGLRFKLQ
NOXA1inhib   FDQAVTKDTCMALGFFQRGVANFQLARFQEALSDFWLALEQLRGHAAIDYTQLGLRFKLQ
NOXA1trunc   FDQAVTKDTCMAVGFFQRGVANFQLARFQEALSDFWLALEQLRGHAAIDYTQLGLRFKLQ
             ............................................................
                           Exon 2                        Exon 3
             121                                            169         180
             |                                              |           |
NOXA1        AWEVLHNVASAQCQLGLWTEAASSLREAMSKWPEGSLNGLDSALDQVQRRGSLPPRQVPR
NOXA1inhib   AWEVLHNVASAQCQLGLWTEATSSLREAMSKWPEGSLNGLDSALDQVQ------------
NOXA1trunc   AWEVLHNVASAQCQLGLWTEAASSLREAMSKWPEGSLNGLDSALDQVQRRGSLPPRQVPR
             ............................................................
                                       Exon 4
             181                                    224                 240
             |                                      |                   |
NOXA1        GEVFRPHRWHLKHLEPVDFLGKAKVVASAIPDDQGWGVRPQQPQGPGANHDARSLIMDSP
NOXA1inhib   --------------------------------------------GPGANHDARSLIMDSP
NOXA1trunc   GEVFRPHRWHLKHLEPVDFLGKAKVVASAIPDDQGWGVRPQQPQGPGANHDARSLIMDSP
             ............................................................
                         Exon 5                  Exon 6        Exon 7
             241                          273                          300
             |                            |                            |
NOXA1        RAGTHQGPLDAETEVGADRCTSTAYQEQRPQVEQVGKQAPLSPGLPAMGGPGPGPCEDPA
NOXA1inhib   RAGTHQGPLDAETEVGADRCTSTAYQEQRPQVEQVGKQAPLSPGLLAMGGPGPGPCEDPA
NOXA1trunc   RAGTHQGPLDAETEVGADRCASTAYQEQRPQVE
             ............................................................
                            Exon 8              Exon 9        Exon 10
             301                                                         360
             |                          PB1                              |
NOXA1        GAGGAGAGGSEPLVTVTVQCAFTVALRARRGADLSSLRALLGQALPHQAQLGQLSYLAPG
NOXA1inhib   GAGGAGAGGSEPLVTVTVQRAFTVALRARRGADLSSLRALLGQALPHQAQLGQLSYLAPG
NOXA1trunc
             ............................................................
                                       Exon 11
             361                       393                    SH3       420
             |                         |                                |
NOXA1        EDGHWVPIPEEESLQRAWQDAAACPRGLQLQCRGAGGRPVLY QVVAQHSYSAQGPEDLGF
NOXA1inhib   EDGHWVPIPEEESLQRAWQDAAACPRGLQLQCRGAGGRPVLY QVVAQHSYSAQGPEDLGF
NOXA1trunc
             ............................................................
                                Exon 12                         Exon 13
             421    431                                                 473
             |      |                                                   |
NOXA1        RQGDTVDVLCE-------VDQAWLEGHCDGRIGIFPKCFVVPAGPRMSGAPGRLPRSQQG
NOXA1inhib   RQGDTVDVLCEEPDVPLAVDQAWLEGHCDGRIGIFPKCFVVPAGPRMSGAPGRLPRSQQG
NOXA1trunc
             ............................................................
                                             Exon 14
             476
             |
NOXA1        DQP
NOXA1inhib   DQP
NOXA1trunc
```

Figure 4
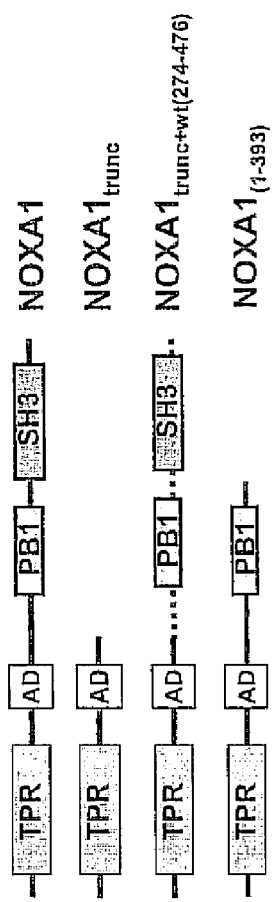
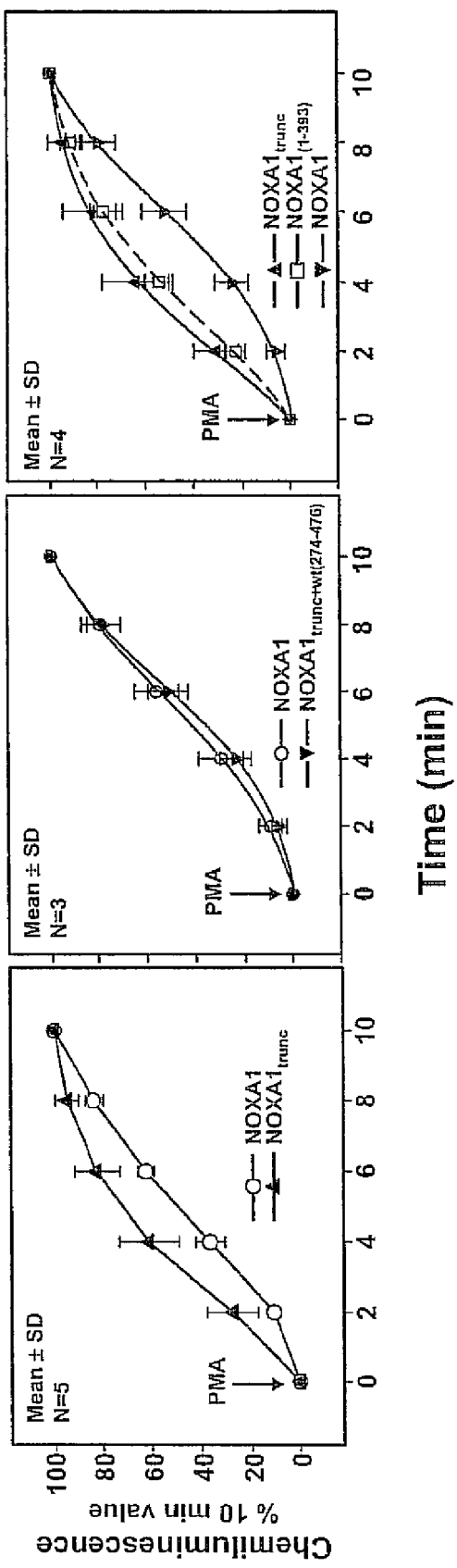

SEQUENCE LISTING

<160> NUMBER OF SEQ ID NOS: 33

<210> SEQ ID NO 1
<211> LENGTH: 476
<212> TYPE: PRT
<213> ORGANISM: Homo sapiens
<220> FEATURE:
<221> NAME/KEY: misc_feature
<223> OTHER INFORMATION: NADPH oxidase activator 1 (NOXA1)
<300> PUBLICATION INFORMATION:
<301> AUTHORS: Geiszt,M., Lekstrom,K., Witta,J. and Leto,T.L.
<302> TITLE: Proteins Homologous to p47phox and p67phox Support
       Superoxide Production by NAD(P)H Oxidase 1 in Colon Epithelial
       Cells
<303> JOURNAL: Journal of Biological Chemistry
<304> VOLUME: 278
<305> ISSUE: 22
<306> PAGES: 20006-20012
<307> DATE: 2003-03-25

<400> SEQUENCE: 1

Met Ala Ser Leu Gly Asp Leu Val Arg Ala Trp His Leu Gly Ala Gln
1               5                   10                  15

Ala Val Asp Arg Gly Asp Trp Ala Arg Ala Leu His Leu Phe Ser Gly
            20                  25                  30

Val Pro Ala Pro Pro Ala Arg Leu Cys Phe Asn Ala Gly Cys Val His
        35                  40                  45

Leu Leu Ala Gly Asp Pro Glu Ala Ala Leu Arg Ala Phe Asp Gln Ala
    50                  55                  60

Val Thr Lys Asp Thr Cys Met Ala Val Gly Phe Phe Gln Arg Gly Val
65                  70                  75                  80

Ala Asn Phe Gln Leu Ala Arg Phe Gln Glu Ala Leu Ser Asp Phe Trp
                85                  90                  95

Leu Ala Leu Glu Gln Leu Arg Gly His Ala Ala Ile Asp Tyr Thr Gln
            100                 105                 110

Leu Gly Leu Arg Phe Lys Leu Gln Ala Trp Glu Val Leu His Asn Val
        115                 120                 125

Ala Ser Ala Gln Cys Gln Leu Gly Leu Trp Thr Glu Ala Ala Ser Ser
    130                 135                 140

Leu Arg Glu Ala Met Ser Lys Trp Pro Glu Gly Ser Leu Asn Gly Leu
145                 150                 155                 160

Asp Ser Ala Leu Asp Gln Val Gln Arg Gly Ser Leu Pro Pro Arg
                165                 170                 175

Gln Val Pro Arg Gly Glu Val Phe Arg Pro His Arg Trp His Leu Lys
            180                 185                 190

His Leu Glu Pro Val Asp Phe Leu Gly Lys Ala Lys Val Val Ala Ser
        195                 200                 205

Ala Ile Pro Asp Asp Gln Gly Trp Gly Val Arg Pro Gln Gln Pro Gln
    210                 215                 220

Gly Pro Gly Ala Asn His Asp Ala Arg Ser Leu Ile Met Asp Ser Pro
225                 230                 235                 240

Arg Ala Gly Thr His Gln Gly Pro Leu Asp Ala Glu Thr Glu Val Gly
                245                 250                 255

Ala Asp Arg Cys Thr Ser Thr Ala Tyr Gln Glu Gln Arg Pro Gln Val

-continued

```
                260                 265                 270
Glu Gln Val Gly Lys Gln Ala Pro Leu Ser Pro Gly Leu Pro Ala Met
            275                 280                 285
Gly Gly Pro Gly Pro Gly Pro Cys Glu Asp Pro Ala Gly Ala Gly Gly
        290                 295                 300
Ala Gly Ala Gly Gly Ser Glu Pro Leu Val Thr Val Thr Val Gln Cys
305                 310                 315                 320
Ala Phe Thr Val Ala Leu Arg Ala Arg Arg Gly Ala Asp Leu Ser Ser
                325                 330                 335
Leu Arg Ala Leu Leu Gly Gln Ala Leu Pro His Gln Ala Gln Leu Gly
            340                 345                 350
Gln Leu Ser Tyr Leu Ala Pro Gly Glu Asp Gly His Trp Val Pro Ile
        355                 360                 365
Pro Glu Glu Glu Ser Leu Gln Arg Ala Trp Gln Asp Ala Ala Ala Cys
    370                 375                 380
Pro Arg Gly Leu Gln Leu Gln Cys Arg Gly Ala Gly Gly Arg Pro Val
385                 390                 395                 400
Leu Tyr Gln Val Val Ala Gln His Ser Tyr Ser Ala Gln Gly Pro Glu
                405                 410                 415
Asp Leu Gly Phe Arg Gln Gly Asp Thr Val Asp Val Leu Cys Glu Val
            420                 425                 430
Asp Gln Ala Trp Leu Glu Gly His Cys Asp Gly Arg Ile Gly Ile Phe
        435                 440                 445
Pro Lys Cys Phe Val Val Pro Ala Gly Pro Arg Met Ser Gly Ala Pro
    450                 455                 460
Gly Arg Leu Pro Arg Ser Gln Gln Gly Asp Gln Pro
465                 470                 475

<210> SEQ ID NO 2
<211> LENGTH: 427
<212> TYPE: PRT
<213> ORGANISM: Artificial
<220> FEATURE:
<223> OTHER INFORMATION: EPDVPLA inserted at 431 of NOXA1
      deletion of NOXA1 exons 5 and 6

<400> SEQUENCE: 2

Met Ala Ser Leu Gly Asp Leu Val Arg Ala Trp His Leu Gly Ala Gln
1               5                   10                  15
Ala Val Asp Arg Gly Asp Trp Ala Arg Ala Leu His Leu Phe Ser Gly
            20                  25                  30
Val Pro Ala Pro Pro Ala Arg Leu Cys Phe Asn Ala Gly Cys Val His
        35                  40                  45
Leu Leu Ala Gly Asp Pro Glu Ala Ala Leu Arg Ala Phe Asp Gln Ala
    50                  55                  60
Val Thr Lys Asp Thr Cys Met Ala Val Gly Phe Phe Gln Arg Gly Val
65                  70                  75                  80
Ala Asn Phe Gln Leu Ala Arg Phe Gln Glu Ala Leu Ser Asp Phe Trp
                85                  90                  95
Leu Ala Leu Glu Gln Leu Arg Gly His Ala Ala Ile Asp Tyr Thr Gln
            100                 105                 110
Leu Gly Leu Arg Phe Lys Leu Gln Ala Trp Glu Val Leu His Asn Val
        115                 120                 125
Ala Ser Ala Gln Cys Gln Leu Gly Leu Trp Thr Glu Ala Ala Ser Ser
    130                 135                 140
```

```
Leu Arg Glu Ala Met Ser Lys Trp Pro Glu Gly Ser Leu Asn Gly Leu
145                 150                 155                 160

Asp Ser Ala Leu Asp Gln Val Gln Gly Pro Gly Ala Asn His Asp Ala
            165                 170                 175

Arg Ser Leu Ile Met Asp Ser Pro Arg Ala Gly Thr His Gln Gly Pro
            180                 185                 190

Leu Asp Ala Glu Thr Glu Val Gly Ala Asp Arg Cys Thr Ser Thr Ala
            195                 200                 205

Tyr Gln Glu Gln Arg Pro Gln Val Glu Gln Val Gly Lys Gln Ala Pro
            210                 215                 220

Leu Ser Pro Gly Leu Pro Ala Met Gly Gly Pro Gly Pro Gly Pro Cys
225                 230                 235                 240

Glu Asp Pro Ala Gly Ala Gly Gly Ala Gly Ala Gly Gly Ser Glu Pro
            245                 250                 255

Leu Val Thr Val Thr Val Gln Cys Ala Phe Thr Val Ala Leu Arg Ala
            260                 265                 270

Arg Arg Gly Ala Asp Leu Ser Ser Leu Arg Ala Leu Leu Gly Gln Ala
            275                 280                 285

Leu Pro His Gln Ala Gln Leu Gly Gln Leu Ser Tyr Leu Ala Pro Gly
            290                 295                 300

Glu Asp Gly His Trp Val Pro Ile Pro Glu Glu Ser Leu Gln Arg
305                 310                 315                 320

Ala Trp Gln Asp Ala Ala Ala Cys Pro Arg Gly Leu Gln Leu Gln Cys
            325                 330                 335

Arg Gly Ala Gly Gly Arg Pro Val Leu Tyr Gln Val Val Ala Gln His
            340                 345                 350

Ser Tyr Ser Ala Gln Gly Pro Glu Asp Leu Gly Phe Arg Gln Gly Asp
            355                 360                 365

Thr Val Asp Val Leu Cys Glu Glu Pro Asp Val Pro Leu Ala Val Asp
            370                 375                 380

Gln Ala Trp Leu Glu Gly His Cys Asp Gly Arg Ile Gly Ile Phe Pro
385                 390                 395                 400

Lys Cys Phe Val Val Pro Ala Gly Pro Arg Met Ser Gly Ala Pro Gly
            405                 410                 415

Arg Leu Pro Arg Ser Gln Gln Gly Asp Gln Pro
            420                 425

<210> SEQ ID NO 3
<211> LENGTH: 483
<212> TYPE: PRT
<213> ORGANISM: Artificial
<220> FEATURE:
<223> OTHER INFORMATION: EPDVPLA inserted at 431 of NOXA1
      20 NOXA1 R ? C

<400> SEQUENCE: 3

Met Ala Ser Leu Gly Asp Leu Val Arg Ala Trp His Leu Gly Ala Gln
1               5                   10                  15

Ala Val Asp Cys Gly Asp Trp Ala Arg Ala Leu His Leu Phe Ser Gly
            20                  25                  30

Val Pro Ala Pro Pro Ala Arg Leu Cys Phe Asn Ala Gly Cys Val His
            35                  40                  45

Leu Leu Ala Gly Asp Pro Glu Ala Ala Leu Arg Ala Phe Asp Gln Ala
            50                  55                  60

Val Thr Lys Asp Thr Cys Met Ala Val Gly Phe Phe Gln Arg Gly Val
65                  70                  75                  80
```

```
Ala Asn Phe Gln Leu Ala Arg Phe Gln Glu Ala Leu Ser Asp Phe Trp
                85                  90                  95

Leu Ala Leu Glu Gln Leu Arg Gly His Ala Ala Ile Asp Tyr Thr Gln
            100                 105                 110

Leu Gly Leu Arg Phe Lys Leu Gln Ala Trp Glu Val Leu His Asn Val
            115                 120                 125

Ala Ser Ala Gln Cys Gln Leu Gly Leu Trp Thr Glu Ala Ala Ser Ser
        130                 135                 140

Leu Arg Glu Ala Met Ser Lys Trp Pro Glu Gly Ser Leu Asn Gly Leu
145                 150                 155                 160

Asp Ser Ala Leu Asp Gln Val Gln Arg Gly Ser Leu Pro Pro Arg
                165                 170                 175

Gln Val Pro Arg Gly Glu Val Phe Arg Pro His Arg Trp His Leu Lys
                180                 185                 190

His Leu Glu Pro Val Asp Phe Leu Gly Lys Ala Lys Val Val Ala Ser
            195                 200                 205

Ala Ile Pro Asp Asp Gln Gly Trp Gly Val Arg Pro Gln Gln Pro Gln
        210                 215                 220

Gly Pro Gly Ala Asn His Asp Ala Arg Ser Leu Ile Met Asp Ser Pro
225                 230                 235                 240

Arg Ala Gly Thr His Gln Gly Pro Leu Asp Ala Glu Thr Glu Val Gly
                245                 250                 255

Ala Asp Arg Cys Thr Ser Thr Ala Tyr Gln Glu Gln Arg Pro Gln Val
            260                 265                 270

Glu Gln Val Gly Lys Gln Ala Pro Leu Ser Pro Gly Leu Pro Ala Met
            275                 280                 285

Gly Gly Pro Gly Pro Gly Pro Cys Glu Asp Pro Ala Gly Ala Gly Gly
        290                 295                 300

Ala Gly Ala Gly Gly Ser Glu Pro Leu Val Thr Val Thr Val Gln Cys
305                 310                 315                 320

Ala Phe Thr Val Ala Leu Arg Ala Arg Gly Ala Asp Leu Ser Ser
                325                 330                 335

Leu Arg Ala Leu Leu Gly Gln Ala Leu Pro His Gln Ala Gln Leu Gly
            340                 345                 350

Gln Leu Ser Tyr Leu Ala Pro Gly Glu Asp Gly His Trp Val Pro Ile
        355                 360                 365

Pro Glu Glu Glu Ser Leu Gln Arg Ala Trp Gln Asp Ala Ala Ala Cys
        370                 375                 380

Pro Arg Gly Leu Gln Leu Gln Cys Arg Gly Ala Gly Arg Pro Val
385                 390                 395                 400

Leu Tyr Gln Val Val Ala Gln His Ser Tyr Ser Ala Gln Gly Pro Glu
                405                 410                 415

Asp Leu Gly Phe Arg Gln Gly Asp Thr Val Asp Val Leu Cys Glu Glu
                420                 425                 430

Pro Asp Val Pro Leu Ala Val Asp Gln Ala Trp Leu Glu Gly His Cys
            435                 440                 445

Asp Gly Arg Ile Gly Ile Phe Pro Lys Cys Phe Val Val Pro Ala Gly
        450                 455                 460

Pro Arg Met Ser Gly Ala Pro Gly Arg Leu Pro Arg Ser Gln Gln Gly
465                 470                 475                 480

Asp Gln Pro
```

<210> SEQ ID NO 4
<211> LENGTH: 483
<212> TYPE: PRT
<213> ORGANISM: Artificial
<220> FEATURE:
<223> OTHER INFORMATION: EPDVPLA inserted at 431 of NOXA1

<400> SEQUENCE: 4

```
Met Ala Ser Leu Gly Asp Leu Val Arg Ala Trp His Leu Gly Ala Gln
1               5                   10                  15

Ala Val Asp Arg Gly Asp Trp Ala Arg Ala Leu His Leu Phe Ser Gly
            20                  25                  30

Val Pro Ala Pro Pro Ala Arg Leu Cys Phe Asn Ala Gly Cys Val His
        35                  40                  45

Leu Leu Ala Gly Asp Pro Glu Ala Ala Leu Arg Ala Phe Asp Gln Ala
    50                  55                  60

Val Thr Lys Asp Thr Cys Met Ala Val Gly Phe Phe Gln Arg Gly Val
65                  70                  75                  80

Ala Asn Phe Gln Leu Ala Arg Phe Gln Glu Ala Leu Ser Asp Phe Trp
                85                  90                  95

Leu Ala Leu Glu Gln Leu Arg Gly His Ala Ala Ile Asp Tyr Thr Gln
            100                 105                 110

Leu Gly Leu Arg Phe Lys Leu Gln Ala Trp Glu Val Leu His Asn Val
        115                 120                 125

Ala Ser Ala Gln Cys Gln Leu Gly Leu Trp Thr Glu Ala Ala Ser Ser
    130                 135                 140

Leu Arg Glu Ala Met Ser Lys Trp Pro Glu Gly Ser Leu Asn Gly Leu
145                 150                 155                 160

Asp Ser Ala Leu Asp Gln Val Gln Arg Arg Gly Ser Leu Pro Pro Arg
                165                 170                 175

Gln Val Pro Arg Gly Glu Val Phe Arg Pro His Arg Trp His Leu Lys
            180                 185                 190

His Leu Glu Pro Val Asp Phe Leu Gly Lys Ala Lys Val Val Ala Ser
        195                 200                 205

Ala Ile Pro Asp Asp Gln Gly Trp Gly Val Arg Pro Gln Gln Pro Gln
    210                 215                 220

Gly Pro Gly Ala Asn His Asp Ala Arg Ser Leu Ile Met Asp Ser Pro
225                 230                 235                 240

Arg Ala Gly Thr His Gln Gly Pro Leu Asp Ala Glu Thr Glu Val Gly
                245                 250                 255

Ala Asp Arg Cys Thr Ser Thr Ala Tyr Gln Glu Gln Arg Pro Gln Val
            260                 265                 270

Glu Gln Val Gly Lys Gln Ala Pro Leu Ser Pro Gly Leu Pro Ala Met
        275                 280                 285

Gly Gly Pro Gly Pro Gly Pro Cys Glu Asp Pro Ala Gly Ala Gly Gly
    290                 295                 300

Ala Gly Ala Gly Gly Ser Glu Pro Leu Val Thr Val Thr Val Gln Cys
305                 310                 315                 320

Ala Phe Thr Val Ala Leu Arg Ala Arg Arg Gly Ala Asp Leu Ser Ser
                325                 330                 335

Leu Arg Ala Leu Leu Gly Gln Ala Leu Pro His Gln Ala Gln Leu Gly
            340                 345                 350

Gln Leu Ser Tyr Leu Ala Pro Gly Glu Asp Gly His Trp Val Pro Ile
        355                 360                 365

Pro Glu Glu Glu Ser Leu Gln Arg Ala Trp Gln Asp Ala Ala Ala Cys
```

-continued

```
               370                 375                 380
Pro Arg Gly Leu Gln Leu Gln Cys Arg Gly Ala Gly Gly Arg Pro Val
385                 390                 395                 400

Leu Tyr Gln Val Val Ala Gln His Ser Tyr Ser Ala Gln Gly Pro Glu
                405                 410                 415

Asp Leu Gly Phe Arg Gln Gly Asp Thr Val Asp Val Leu Cys Glu Glu
                420                 425                 430

Pro Asp Val Pro Leu Ala Val Asp Gln Ala Trp Leu Glu Gly His Cys
                435                 440                 445

Asp Gly Arg Ile Gly Ile Phe Pro Lys Cys Phe Val Val Pro Ala Gly
450                 455                 460

Pro Arg Met Ser Gly Ala Pro Gly Arg Leu Pro Arg Ser Gln Gln Gly
465                 470                 475                 480

Asp Gln Pro
```

<210> SEQ ID NO 5
<211> LENGTH: 526
<212> TYPE: PRT
<213> ORGANISM: Homo sapiens
<220> FEATURE:
<221> NAME/KEY: misc_feature
<223> OTHER INFORMATION: p67phox-like protein
<300> PUBLICATION INFORMATION:
<301> AUTHORS: Yoshida,L.S., Nishida,S., Shimoyama,T., Kawahara,T.,
       Rokutan,K. and Tsunawaki,S.
<302> TITLE: Expression of a p67phox homolog in Caco-2 cells giving
       O2(-)-reconstituting ability to cytochrome b558 together with
       recombinant p47phox
<303> JOURNAL: Biochem. Biophys. Res. Commun.
<304> VOLUME: 296
<305> ISSUE: 5
<306> PAGES: 1322-1328
<307> DATE: 2002-09

<400> SEQUENCE: 5

```
Met Ser Leu Val Glu Ala Ile Ser Leu Trp Asn Glu Gly Val Leu Ala
1               5                   10                  15

Ala Asp Lys Lys Asp Trp Lys Gly Ala Leu Asp Ala Phe Ser Ala Val
                20                  25                  30

Gln Asp Pro His Ser Arg Ile Cys Phe Asn Ile Gly Cys Met Tyr Thr
            35                  40                  45

Ile Leu Lys Asn Met Thr Glu Ala Glu Lys Ala Phe Thr Arg Ser Ile
50                  55                  60

Asn Arg Asp Lys His Leu Ala Val Ala Tyr Phe Gln Arg Gly Met Leu
65                  70                  75                  80

Tyr Tyr Gln Thr Glu Lys Tyr Asp Leu Ala Ile Lys Asp Leu Lys Glu
                85                  90                  95

Ala Leu Ile Gln Leu Arg Gly Asn Gln Leu Ile Asp Tyr Lys Ile Leu
            100                 105                 110

Gly Leu Gln Phe Lys Leu Phe Ala Cys Glu Val Leu Tyr Asn Ile Ala
            115                 120                 125

Phe Met Tyr Ala Lys Lys Glu Glu Trp Lys Lys Ala Glu Glu Gln Leu
            130                 135                 140

Ala Leu Ala Thr Ser Met Lys Ser Glu Pro Arg His Ser Lys Ile Asp
145                 150                 155                 160

Lys Ala Met Glu Cys Val Trp Lys Gln Lys Leu Tyr Glu Pro Val Val
                165                 170                 175

Ile Pro Val Gly Arg Leu Phe Arg Pro Asn Glu Arg Gln Val Ala Gln
            180                 185                 190
```

```
Leu Ala Lys Lys Asp Tyr Leu Gly Lys Ala Thr Val Val Ala Ser Val
            195                 200                 205

Val Asp Gln Asp Ser Phe Ser Gly Phe Ala Pro Leu Gln Pro Gln Ala
210                 215                 220

Ala Glu Pro Pro Pro Arg Pro Lys Thr Pro Glu Ile Phe Arg Ala Leu
225                 230                 235                 240

Glu Gly Glu Ala His Arg Val Leu Phe Gly Phe Val Pro Glu Thr Lys
            245                 250                 255

Glu Glu Leu Gln Val Met Pro Gly Asn Ile Val Phe Val Leu Lys Lys
            260                 265                 270

Gly Asn Asp Asn Trp Ala Thr Val Met Phe Asn Gly Gln Lys Gly Leu
            275                 280                 285

Val Pro Cys Asn Tyr Leu Glu Pro Val Glu Leu Arg Ile His Pro Gln
            290                 295                 300

Gln Gln Pro Gln Glu Glu Ser Ser Pro Gln Ser Asp Ile Pro Ala Pro
305                 310                 315                 320

Pro Ser Ser Lys Ala Pro Gly Arg Pro Gln Leu Ser Pro Gly Gln Lys
            325                 330                 335

Gln Lys Glu Glu Pro Lys Glu Val Lys Leu Ser Val Pro Met Pro Tyr
            340                 345                 350

Thr Leu Lys Val His Tyr Lys Tyr Thr Val Val Met Lys Thr Gln Pro
            355                 360                 365

Gly Leu Pro Tyr Ser Gln Val Arg Asp Met Val Ser Lys Lys Leu Glu
            370                 375                 380

Leu Arg Leu Glu His Thr Lys Leu Ser Tyr Arg Pro Arg Asp Ser Asn
385                 390                 395                 400

Glu Leu Val Pro Leu Ser Glu Asp Ser Met Lys Asp Ala Trp Gly Gln
                405                 410                 415

Val Lys Asn Tyr Cys Leu Thr Leu Trp Cys Glu Asn Thr Val Gly Asp
                420                 425                 430

Gln Gly Phe Pro Asp Glu Pro Lys Glu Ser Glu Lys Ala Asp Ala Asn
                435                 440                 445

Asn Gln Thr Thr Glu Pro Gln Leu Lys Lys Gly Ser Gln Val Glu Ala
450                 455                 460

Leu Phe Ser Tyr Glu Ala Thr Gln Pro Glu Asp Leu Glu Phe Gln Glu
465                 470                 475                 480

Gly Asp Ile Ile Leu Val Leu Ser Lys Val Asn Glu Glu Trp Leu Glu
                485                 490                 495

Gly Glu Cys Lys Gly Lys Val Gly Ile Phe Pro Lys Val Phe Val Glu
                500                 505                 510

Asp Cys Ala Thr Thr Asp Leu Glu Ser Thr Arg Arg Glu Val
                515                 520                 525

<210> SEQ ID NO 6
<211> LENGTH: 5
<212> TYPE: PRT
<213> ORGANISM: Artificial
<220> FEATURE:
<223> OTHER INFORMATION: insertion sequence in NOXA1 or p67phox

<400> SEQUENCE: 6

Pro His Val Gly Ala
1               5

<210> SEQ ID NO 7
```

```
<211> LENGTH: 7
<212> TYPE: PRT
<213> ORGANISM: Artificial
<220> FEATURE:
<223> OTHER INFORMATION: insertion sequence in NOXA1 or p67phox

<400> SEQUENCE: 7

Glu Pro Asp Val Pro Leu Ala
1               5

<210> SEQ ID NO 8
<211> LENGTH: 10
<212> TYPE: PRT
<213> ORGANISM: Artificial
<220> FEATURE:
<223> OTHER INFORMATION: insertion sequence in NOXA1 or p67phox

<400> SEQUENCE: 8

Phe Val Pro Val Asp Ser Lys Glu Ala His
1               5                   10

<210> SEQ ID NO 9
<211> LENGTH: 13
<212> TYPE: PRT
<213> ORGANISM: Human immunodeficiency virus
<220> FEATURE:
<221> NAME/KEY: misc_feature
<223> OTHER INFORMATION: TAT 48-60

<400> SEQUENCE: 9

Gly Arg Lys Lys Arg Arg Gln Arg Arg Arg Pro Pro Gln
1               5                   10

<210> SEQ ID NO 10
<211> LENGTH: 13
<212> TYPE: PRT
<213> ORGANISM: Human immunodeficiency virus
<220> FEATURE:
<221> NAME/KEY: misc_feature
<223> OTHER INFORMATION: R9-Tat

<400> SEQUENCE: 10

Gly Arg Arg Arg Arg Arg Arg Arg Arg Arg Pro Pro Gln
1               5                   10

<210> SEQ ID NO 11
<211> LENGTH: 17
<212> TYPE: PRT
<213> ORGANISM: Human immunodeficiency virus
<220> FEATURE:
<221> NAME/KEY: misc_feature
<223> OTHER INFORMATION: HIV-1 Rev 34-50

<400> SEQUENCE: 11

Thr Arg Gln Ala Arg Arg Asn Arg Arg Arg Trp Arg Glu Arg Gln
1               5                   10                  15

Arg

<210> SEQ ID NO 12
<211> LENGTH: 15
<212> TYPE: PRT
<213> ORGANISM: flock house virus
<220> FEATURE:
<221> NAME/KEY: misc_feature
<223> OTHER INFORMATION: FHV coat 35-49

<400> SEQUENCE: 12
```

```
Arg Arg Arg Arg Asn Arg Thr Arg Arg Asn Arg Arg Arg Val Arg
1               5                   10                  15
```

<210> SEQ ID NO 13
<211> LENGTH: 19
<212> TYPE: PRT
<213> ORGANISM: Brome mosaic virus
<220> FEATURE:
<221> NAME/KEY: misc_feature
<223> OTHER INFORMATION: gag 7-25

<400> SEQUENCE: 13

```
Lys Met Thr Arg Ala Gln Arg Arg Ala Ala Ala Arg Arg Asn Arg Trp
1               5                   10                  15

Thr Ala Arg
```

<210> SEQ ID NO 14
<211> LENGTH: 13
<212> TYPE: PRT
<213> ORGANISM: Human T-cell lymphotropic virus type 2
<220> FEATURE:
<221> NAME/KEY: misc_feature
<223> OTHER INFORMATION: HTLV-II Rex 4-16

<400> SEQUENCE: 14

```
Thr Arg Arg Gln Arg Thr Arg Arg Ala Arg Arg Asn Arg
1               5                   10
```

<210> SEQ ID NO 15
<211> LENGTH: 16
<212> TYPE: PRT
<213> ORGANISM: Drosophilia atennapedia
<220> FEATURE:
<221> NAME/KEY: misc_feature
<223> OTHER INFORMATION: pentratin 43-58

<400> SEQUENCE: 15

```
Arg Gln Ile Lys Ile Trp Phe Gln Asn Arg Arg Met Lys Trp Lys Lys
1               5                   10                  15
```

<210> SEQ ID NO 16
<211> LENGTH: 26
<212> TYPE: PRT
<213> ORGANISM: Unknown
<220> FEATURE:
<223> OTHER INFORMATION: transportan

<400> SEQUENCE: 16

```
Leu Ile Lys Lys Ala Leu Ala Ala Leu Ala Lys Leu Asn Ile Lys Leu
1               5                   10                  15

Leu Tyr Gly Ala Ser Asn Leu Thr Trp Gly
            20                  25
```

<210> SEQ ID NO 17
<211> LENGTH: 27
<212> TYPE: PRT
<213> ORGANISM: Unknown
<220> FEATURE:
<223> OTHER INFORMATION: transportan

<400> SEQUENCE: 17

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

```
<210> SEQ ID NO 18
<211> LENGTH: 24
<212> TYPE: PRT
<213> ORGANISM: Unknown
<220> FEATURE:
<223> OTHER INFORMATION: transportan

<400> SEQUENCE: 18

Leu Asn Ser Ala Gly Tyr Leu Leu Gly Lys Ile Asn Leu Lys Ala Leu
1               5                   10                  15
Ala Ala Leu Ala Lys Lys Ile Leu
            20

<210> SEQ ID NO 19
<211> LENGTH: 25
<212> TYPE: PRT
<213> ORGANISM: Unknown
<220> FEATURE:
<223> OTHER INFORMATION: transportan

<400> SEQUENCE: 1

Gly Trp Thr Leu Asn Ser Ala Gly Tyr Leu Leu Gly Lys Leu Lys Ala
1               5                   10                  15
Leu Ala Ala Leu Ala Lys Lys Ile Leu
            20                  25

<210> SEQ ID NO 20
<211> LENGTH: 21
<212> TYPE: PRT
<213> ORGANISM: Unknown
<220> FEATURE:
<223> OTHER INFORMATION: transportan

<400> SEQUENCE: 20

Ala Gly Tyr Leu Leu Gly Lys Ile Asn Leu Lys Ala Leu Ala Ala Leu
1               5                   10                  15
Ala Lys Lys Ile Leu
            20

<210> SEQ ID NO 21
<211> LENGTH: 22
<212> TYPE: PRT
<213> ORGANISM: Unknown
<220> FEATURE:
<223> OTHER INFORMATION: transportan

<400> SEQUENCE: 21

Leu Asn Ser Ala Gly Tyr Leu Leu Gly Lys Leu Lys Ala Leu Ala Ala
1               5                   10                  15
Leu Ala Lys Lys Ile Leu
            20

<210> SEQ ID NO 22
<211> LENGTH: 19
<212> TYPE: PRT
<213> ORGANISM: Unknown
<220> FEATURE:
<223> OTHER INFORMATION: transportan

<400> SEQUENCE: 22

Ala Gly Tyr Leu Leu Gly Lys Leu Lys Ala Leu Ala Ala Leu Ala Lys
1               5                   10                  15
Lys Ile Leu
```

<210> SEQ ID NO 23
<211> LENGTH: 21
<212> TYPE: DNA
<213> ORGANISM: Artificial
<220> FEATURE:
<223> OTHER INFORMATION: NOXA1 sense primer

<400> SEQUENCE: 23
ccggcccctc cgcgggatcc t                                              21

<210> SEQ ID NO 24
<211> LENGTH: 23
<212> TYPE: DNA
<213> ORGANISM: Artificial
<220> FEATURE:
<223> OTHER INFORMATION: NOXA1 anti-sense primer

<400> SEQUENCE: 24
ttaaaagcat catggacaca gca                                            23

<210> SEQ ID NO 25
<211> LENGTH: 21
<212> TYPE: DNA
<213> ORGANISM: Artificial
<220> FEATURE:
<223> OTHER INFORMATION: NOXA1 sense primer

<400> SEQUENCE: 25
gggatcctgg ccctcctcg a                                               21

<210> SEQ ID NO 26
<211> LENGTH: 22
<212> TYPE: DNA
<213> ORGANISM: Artificial
<220> FEATURE:
<223> OTHER INFORMATION: NOXA1 anti-sense primer

<400> SEQUENCE: 26
gacacagcat cattagggct ga                                             22

<210> SEQ ID NO 27
<211> LENGTH: 26
<212> TYPE: DNA
<213> ORGANISM: Artificial
<220> FEATURE:
<223> OTHER INFORMATION: NOXA1 sense primer

<400> SEQUENCE: 27
cccgggatgg cctctctggg ggacct                                         26

<210> SEQ ID NO 28
<211> LENGTH: 27
<212> TYPE: DNA
<213> ORGANISM: Artificial
<220> FEATURE:
<223> OTHER INFORMATION: NOXA1 anti-sense primer

<400> SEQUENCE: 28
cccgggttag ggctgatctc cctgctg                                        27

<210> SEQ ID NO 29
<211> LENGTH: 24
<212> TYPE: DNA
<213> ORGANISM: Artificial
<220> FEATURE:
<223> OTHER INFORMATION: NOXA1 sense primer
<210> SEQ ID NO 29
<211> LENGTH: 24
<212> TYPE: DNA
<213> ORGANISM: Artificial
<220> FEATURE:
<223> OTHER INFORMATION: NOXA1 sense primer

<400> SEQUENCE: 29
gaattccggg ggtcggccgg tcct                                        24

<210> SEQ ID NO 30
<211> LENGTH: 27
<212> TYPE: DNA
<213> ORGANISM: Artificial
<220> FEATURE:
<223> OTHER INFORMATION: NOXA1 anti-sense primer

<400> SEQUENCE: 30
cccgggttag ggctgatctc cctgctg                                     27

<210> SEQ ID NO 31
<211> LENGTH: 30
<212> TYPE: DNA
<213> ORGANISM: Artificial
<220> FEATURE:
<223> OTHER INFORMATION: NOXA1 sense primer

<400> SEQUENCE: 31
gtgctgctga gctcggaagg gctgggcgct                                  30

<210> SEQ ID NO 32
<211> LENGTH: 20
<212> TYPE: DNA
<213> ORGANISM: Artificial
<220> FEATURE:
<223> OTHER INFORMATION: NOXA1 anti-sense primer

<400> SEQUENCE: 32
tagaaggcac agtcgaggct                                             20

<210> SEQ ID NO 33
<211> LENGTH: 273
<212> TYPE: PRT
<213> ORGANISM: Artificial
<220> FEATURE:
<223> OTHER INFORMATION: 1 .. 273 of NOXA1

<400> SEQUENCE: 33

Met Ala Ser Leu Gly Asp Leu Val Arg Ala Trp His Leu Gly Ala Gln
1               5                   10                  15

Ala Val Asp Arg Gly Asp Trp Ala Arg Ala Leu His Leu Phe Ser Gly
            20                  25                  30

Val Pro Ala Pro Pro Ala Arg Leu Cys Phe Asn Ala Gly Cys Val His
        35                  40                  45

Leu Leu Ala Gly Asp Pro Glu Ala Ala Leu Arg Ala Phe Asp Gln Ala
    50                  55                  60

Val Thr Lys Asp Thr Cys Met Ala Val Gly Phe Phe Gln Arg Gly Val
65                  70                  75                  80

Ala Asn Phe Gln Leu Ala Arg Phe Gln Glu Ala Leu Ser Asp Phe Trp
                85                  90                  95

Leu Ala Leu Glu Gln Leu Arg Gly His Ala Ala Ile Asp Tyr Thr Gln
            100                 105                 110

Leu Gly Leu Arg Phe Lys Leu Gln Ala Trp Glu Val Leu His Asn Val
        115                 120                 125

Ala Ser Ala Gln Cys Gln Leu Gly Leu Trp Thr Glu Ala Ala Ser Ser
    130                 135                 140

Leu Arg Glu Ala Met Ser Lys Trp Pro Glu Gly Ser Leu Asn Gly Leu
145                 150                 155                 160

```
Asp Ser Ala Leu Asp Gln Val Gln Arg Arg Gly Ser Leu Pro Pro Arg
            165                 170                 175

Gln Val Pro Arg Gly Glu Val Phe Arg Pro His Arg Trp His Leu Lys
            180                 185                 190

His Leu Glu Pro Val Asp Phe Leu Gly Lys Ala Lys Val Val Ala Ser
        195                 200                 205

Ala Ile Pro Asp Asp Gln Gly Trp Gly Val Arg Pro Gln Gln Pro Gln
        210                 215                 220

Gly Pro Gly Ala Asn His Asp Ala Arg Ser Leu Ile Met Asp Ser Pro
225                     230                 235                 240

Arg Ala Gly Thr His Gln Gly Pro Leu Asp Ala Glu Thr Glu Val Gly
                245                 250                 255

Ala Asp Arg Cys Thr Ser Thr Ala Tyr Gln Glu Gln Arg Pro Gln Val
            260                 265                 270

Glu
```

US 7,582,606 B2

NADPH OXIDASE CYTOSOLIC COFACTOR MUTANT

CROSS-REFERENCE TO RELATED APPLICATIONS

This application claims priority of U.S. Provisional Patent Application Ser. No. 60/733,101 filed Nov. 3, 2005, which is incorporated herein by reference.

STATEMENT REGARDING FEDERALLY SPONSORED RESEARCH OR DEVELOPMENT

The research carried out in connection with this invention was supported by Grant Nos. AI20866 and AG19519 from the National Institutes of Health.

FIELD OF THE INVENTION

This invention relates to a NADPH oxidase (NOX) cytosolic cofactor NOXA1 or $p67^{phox}$ mutant with an insertion mutation in the SH3 domain alone or in combination with other mutations, a nucleotide sequence coding for the mutant, a vector inclusive of the nucleotide sequence corresponding to the encoded mutant, a cell transformed by such a vector, and a treatment for such disease.

BACKGROUND OF THE INVENTION

The single-electron reduction of molecular oxygen by members of the nicotinamide adenine dinucleotide phosphate (NADPH) oxidase (NOX) family of complex enzymes is an initial step in the generation of reactive oxygen species (ROS) important for a number of biochemical and biological functions. The best studied of the NADPH oxidases, namely that of the peripheral blood phagocytes plays an essential role in the host defense against microbial pathogens. Formation of the stimulus-activated phagocyte NADPH oxidase enzyme complex of NOX species NOX1-4 involves the association of at least four cytosolic subunits: $p47^{phox}$, $p67^{phox}$, $p40^{phox}$, and the small GTPase Rac2; with a core membrane-bound catalytic subunit, flavocytochrome $b_{558}$ that includes a heterodimer of NOX2 (also known as $gp91^{phox}$) and $p22^{phox}$. With the exception of $p40^{phox}$, there is an absolute requirement for each of the subunits for the formation of a functional NOX2 enzyme in vivo. Critical intermediate steps in the activation process are the phosphorylation of multiple serine residues in $p47^{phox}$, which reverses its auto-inhibited state, revealing binding sites for flavocytochrome $b_{558}$, and the activation of Rac2 by the exchange of GDP with GTP. The full assembly of an active phagocyte NADPH oxidase complex is dependent on a number of specific protein binding domains located on each of the subunits (1-3).

The recent discovery in non-phagocytic cells of oxidase core proteins homologous to NOX2 has expanded knowledge of both the role of ROS in biochemical and cellular processes, and the mechanisms of activation of the NOX core proteins (4-11). All NOX family members share the common features of multiple membrane-spanning domains and binding sites for heme, FAD, and NADPH. However it is now emerging that the NOX proteins differ in their modes of activation and requirements for cytosolic cofactors. NOX5, expressed in spermatocytes and lymphoid tissues, has an extended N-terminal domain containing four $Ca^{2+}$-binding, EF-hand motifs (8), Binding of $Ca^{2+}$ by these sites leads to a conformational change in the protein sufficient for the formation of a functional oxidase, apparently without cofactor requirements (12). NOX4 displays a rather wide distribution in tissue, but is particularly well expressed in renal cells (6-10; 13) where it serves as an oxygen sensor regulating erythropoietin production. It has been postulated to serve as an oxygen sensor (6), and has been implicated in the signal transduction pathways mediating the angiotensin II response in glomerular mesangial cells (13), the insulin-receptor mediated response in adipocytes (14), and the endoplasmic reticulum stress response in human aortic smooth muscle cells (15). NOX3 is expressed in fetal kidney (9), and is particularly highly expressed in the inner ear of the mammals (11). NOX3-deficiency in mice is associated with the otoconia-deficient head-tilt phenotype (16). Unique among the NOX proteins, NOX3 appears to function well with either $p47^{phox}$ and $p67^{phox}$ or their recently described homologues, NOXO1 and NOXA1 (11; 17-20). On the other hand, the activation of NOX1, a NOX isoform most highly expressed in colon epithelium, requires NOXA1 and NOXO1, and shows only minimal activity with the cytosolic proteins $p47^{phox}$ and $p67^{phox}$. It has been suggested that the NOX1/NOXO1/NOXA1 oxidase system functions in an antimicrobial capacity, as well as in the regulation of cell growth.

The discovery of the phox protein homologues NOXA1 and NOXO1 has also changed the perspective on how the NOX proteins may be functionally regulated (18-20). Similar to $p47^{phox}$, NOXO1 contains an N-terminal inositide-binding PX domain and the characteristic tandem SH3 domains in its central region. However, the basic region in the C-terminal end responsible for intramolecular binding and the resting auto-inhibited state in $p47^{phox}$ is absent from NOXO1. This difference is likely the basis for the observation that the NOX1/NOXO1/NOXA1 system displays constitutive activity in some cell types, whereas it is inducible in others (18-20). NOXA1, like its homologue $p67^{phox}$, contains in its N-terminal region the complex TPR domain, which is responsible for binding activated (GTP-bound) Rac, an activation domain containing a critical valine, a putative C-terminal PB1 domain and a C-terminal SH3 domain.

In addition to NOXA1, cytosolic cofactor $p67^{phox}$ (19) is also known to be active as a homologue to NOXA1 in the formation of NOX oxidases NOX1-4.

In spite of the considerable knowledge developed regarding NADPH oxidase enzymes the cell type distribution of NOX1-5 in various tissues, and a mechanism of cytochrome $b_{558}$ activation, surprisingly little progress has been made in devising therapeutics that draw on this information. Thus, there exists a need for a NOX cytosolic cofactor having a biological activity different from the wild-type cofactor.

SUMMARY OF THE INVENTION

A purified polypeptide includes an NADPH oxidase cytosolic cofactor polypeptide NOXA1 (SEQ ID NO: 1) or $p67^{phox}$ (SEQ ID NO: 5) having a C-terminal SH3 domain insertion mutation of at least three consecutive amino acids positioned between PEDL (SEQ ID NO: 35) and GIFPK (SEQ ID NO: 34) motifs of said SH3 domain so as to reduce activity of the purified polypeptide relative to the wild-type cofactor polypeptide. A purified polypeptide optionally further includes at least one additional mutation such as a mutation in a cofactor activation domain, a point mutation changing a tyrosine residue within the SH3 domain, or a nonsilent mutation within a PB1 domain of the wild-type cofactor polypeptide.

A purified nucleotide sequence coding for such a purified polypeptide is also provided, the purified nucleotide sequence being amenable to incorporation within an expression vector.

A pharmaceutical composition is disclosed that includes that purified polypeptide and a pharmaceutically acceptable carrier.

A process for treating, inhibiting, or prophylactically preventing a disease associated with the overproduction of reactive oxygen species involving NOXn where n is 1-4 inclusive includes the administration of a therapeutically effective amount with a purified polypeptide to a subject tissue that is overproducing reactive oxygen species through a NOXn pathway.

BRIEF DESCRIPTION OF THE DRAWINGS

FIG. 1 is sequence alignments between the sequence wild-type NOXA1 (SEQ ID NO: 1) and the predicted sequences of NOXA1$_{trunc}$ (SEQ ID NO: 1 residues 1-273+Ala51Thr, Thr261Ala) and NOXA1$_{inhib}$ (SEQ ID NO: 2).

FIG. 4 is a set of plots showing induction kinetics of NOX1 NADPH oxidase activity by wild-type and truncated NOXA1 variants in K562/NOX1/NOXO1 cells transfected with the indicated NOXA1 constructs (see schematics above plot) and PMA-stimulated superoxide activity assayed as in FIG. 3. The data are normalized by subtraction of the zero-time value and then expressed as a percentage of the 10 min values. Left panel, Comparison of NOXA1 (SEQ ID NO: 1) with NOXA1$_{trunc}$ (SEQ ID NO: 1 residues 1-273+Ala51Thr, Thr261Ala). Middle panel, Comparison of NOXA1 (SEQ ID NO: 1) with NOXA1 $_{trunc+wt\ (274-476)}$(SEQ ID NO: 1+Ala51Thr, Thr261Ala). Right panel, Comparison of NOXA1$_{(1-393)}$ (SEQ ID NO: 1 residues 1-393) (wild-type NOXA1 with the SH3 domain deleted) with NOXA1$_{trunc}$ (SEQ ID NO: 1 residues 1-273 Ala51Thr, Thr261Ala) and NOXA1 (SEQ ID NO: 1).

DETAILED DESCRIPTION OF THE PREFERRED EMBODIMENTS

Figure 2:
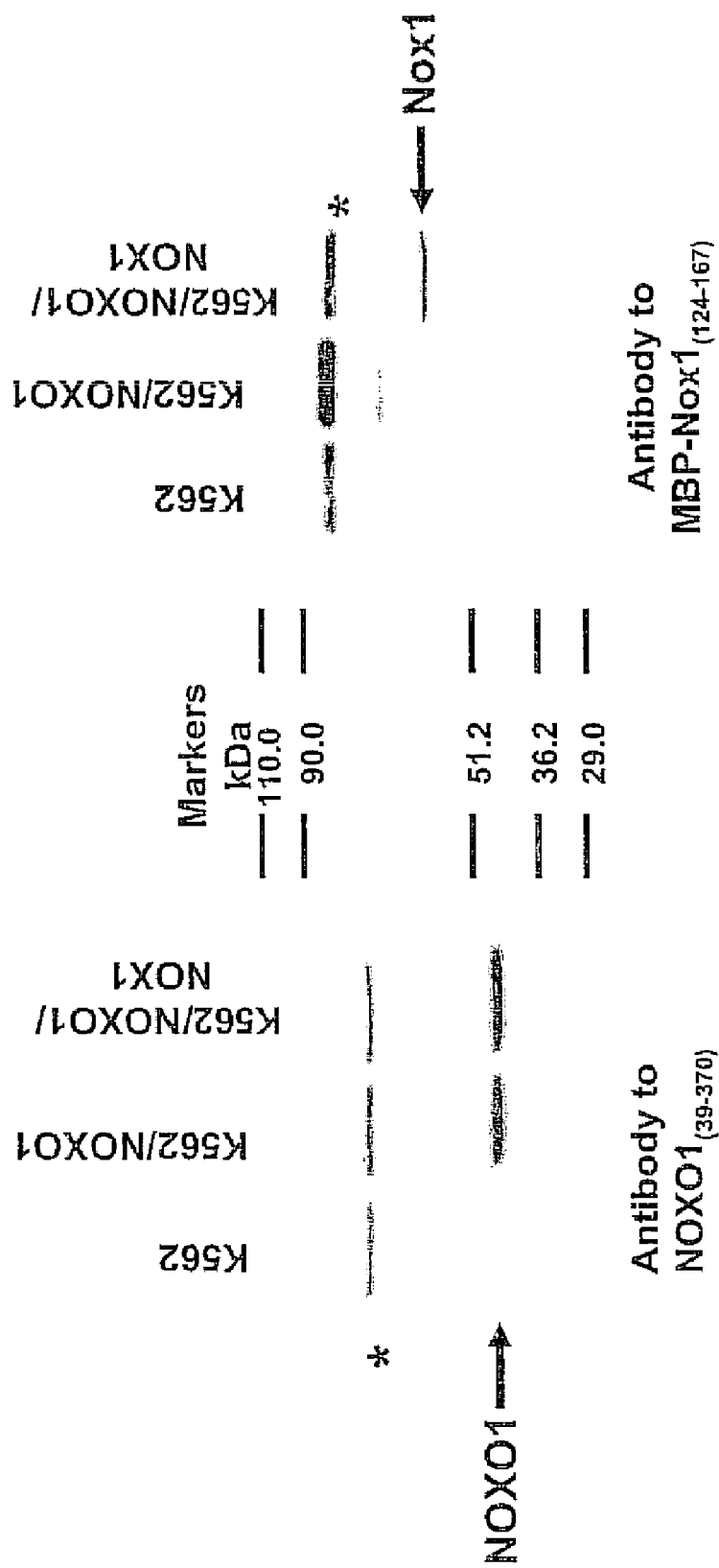
FIG. 2 is an electrophoretic immunodetection gel of NOX1 and NOXO1 in stable transfected K562 cells.

The present invention has utility in the treatment of conditions associated with excess formation of reactive oxygen species by NOX species NOX1-4. Active oxygen species are implicated in a variety of disease processes, and as such the present invention represents a process to ameliorate symptoms associated therewith through kinetic inhibition of NOX activation. Disease states associated with excess reactive oxygen species include pathophysiology of aging; atherosclerosis; neoplastic diseases; diabetes; diabetic retinopathy;

chronic inflammatory diseases of the gastrointestinal tract, including chronic granulomatous disease; aging of skin; Alzheimer's disease and other neurological disorders; and rheumatoid arthritis.

NOXA1 (activator of NOX-1) or the homologue p67$^{phox}$ is active in the biochemical cascade to generate superoxide. Superoxide is a beneficial precursor in the formation of microbiocidal oxidants; however, the excess production of a reactive oxygen species is associated with the aforementioned disorders. According to the present invention, the cytosolic cofactor protein NOXA1 or p67$^{phox}$, through an insertion mutation to introduce into the C-terminal SH3 domain at least a 3 amino acid mutant insert between conservative SH3 domain amino acid sequences PEDL (SEQ ID NO: 35)and GIFPK (SEQ ID NO: 34). The amino acid mutant insert preferably has a net hydropathic index of between −2.4 and 1.6. The reduced relative activity of an inventive polypeptide mutant is manifest as reduced superoxide production in cells expressing or exposed to an inventive polypeptide mutant.

DEFINITIONS

The following definitions are provided to facilitate understanding of terms used in the specification.

The polypeptides and nucleic acid sequences of the present invention are preferably provided in an isolated form, and preferably are purified to homogeneity.

The term "biological activity" as used herein is intended to mean a measurement of the amount of stimulated superoxide generation by a NOX participation with a cytosolic protein NOXA1 or p67$^{phox}$ or an inventive insertion mutant thereof in a period of time measured by appropriate method as shown in Example 5.

The term "mutant" as used herein is intended to mean a modified protein which differs from the wild-type protein.

The term "insertion mutant" as used herein is intended to mean a modified protein which differs from the wild-type protein by the addition of at least a 3 amino acid fragment located within the C-terminal SH3 domain of NOXA1 (SEQ ID NO: 1)or p67$^{phox}$ (SEQ ID NO: 5) between the conserved sequence portions PEDL (SEQ ID NO: 35) and GIFPK (SEQ ID NO: 34).

The term "isolated" is intended to mean that the material is removed from the natural environment in which it occurs, and thus is altered "by the hand of man" from its natural state. By way of example, a naturally-occurring nucleic acid sequence or polypeptide present in a living animal is not isolated, but the same nucleic acid sequence or polypeptide, separated from some or all of the coexisting materials in the natural system, is isolated. Such isolated nucleic acid sequences are optionally part of a vector and/or such nucleic acid sequences or polypeptides are optionally part of a composition, or are contained within a cell, and yet still isolated in that such vector, composition, or particular cell is not part of its original natural environment. The term is not intended to refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the nucleic acid sequences of the present invention.

The term "therapeutically effective amount" as used herein is intended to mean that amount of the compound being administered which will relieve to some extent one or more of the symptoms of the disorder being treated. In reference to excess reactive oxygen species associated disorders, a therapeutically effective amount refers to that amount which has the effect of reducing NOX1, NOX2, NOX3, or NOX4 superoxide generation and relieving to some extent one or more symptoms associated with a pathology related to, or caused in part by the disorder.

"Pharmaceutically acceptable salt" as used herein is intended to mean to those salts which retain the biological effectiveness and properties of the free bases and which are obtained by reaction with inorganic or organic acids, hydrochloric acid, hydrobromic acid, sulfuric acid, nitric acid, phosphoric acid, alkylsulfonic acids, arylsulfonic acids, acetic acid, salicylic acid, malic acid, maleic acid, succinic acid, tartaric acid, or citric acid, or formed with cations derived from sodium, potassium, ammonium, calcium, ferric hydroxides, isopropylamine, triethylamine 2-ethylamino ethanol, histidine or procaine.

A "pharmaceutical composition" as used herein is intended to mean a mixture of one or more of the compounds described herein, or pharmaceutically acceptable salts thereof, with other chemical components, such as physiologically acceptable carriers and excipients. One purpose of a pharmaceutical composition is to facilitate administration of a compound to a subject.

As used herein, a "pharmaceutically acceptable carrier" as used herein is intended to mean a carrier or diluent that does not cause significant irritation to an organism and does not abrogate the biological activity and properties of the administered compound.

An "excipient" as used herein is intended to mean an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Treating" or "treatment" of a disease as used herein is intended to mean preventing the disease from occurring in a subject organism that may be predisposed to the disease, but does not yet experience or exhibit symptoms of the disease (prophylactic treatment); inhibiting the disease (slowing or arresting its development); providing relief from the symptoms or side-effects of the disease (including palliative treatment); and relieving the disease (causing regression of the disease).

An inventive "nucleotide sequence" as used herein is intended to mean a molecule having a nucleic acid sequence coding for an inventive NOXA1 or p67$^{phox}$ polypeptide mutant or a polypeptide fragment as exemplified in SEQ ID NOS. 6-8 inserted between bases 1389 to 1492 (AY255769) of NOXA1 (Accession No. AY255769) or between bases 1450 and 1532 of p67$^{phox}$ (Accession No. AF527950). For example, the inventive nucleotide sequence can contain the nucleotide sequence of the full length cDNA sequence, including the 5' and 3' untranslated sequences, the coding region, with or without the signal sequence, the protein coding region, as well as fragments, epitopes, domains, and variants of the nucleic acid sequence.

An inventive "nucleotide sequence" also includes those nucleotides capable of hybridizing, under stringent hybridization conditions, to sequences coding for an "insertion mutant", the complement thereof, or the cDNA corresponding thereto with the proviso that a sequence only hybridizing a polyA region, complementary T or U repeat sequence is excluded from a nucleotide sequence as defined herein. "Stringent hybridization conditions" refers to an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Also contemplated are nucleotides that hybridize to the insertion mutant nucleotide sequences under less stringent hybridization conditions. Changes in the stringency of hybridization and signal detection are primarily accomplished through the manipulation of formamide concentration, with lower percentages of formamide result in lowered stringency; salt conditions, or temperature. For example, a less stringent set of hybridization conditions include an overnight incubation at 37° C. in a solution comprising 6×SSPE (20×SSPE=3M NaCl; 0.2M NaH$_2$PO$_4$; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). It is appreciated that variations in hybridization conditions may be accomplished through the inclusion and/or substitution of alternate blocking reagents used to suppress background in hybridization experiments.

Inventive NOXA1 or p67$^{phox}$ Mutants

Modifications and changes are optionally made in the structure of an inventive insertion mutant and the corresponding coding nucleotide sequence and still obtain a molecule having similar characteristics to the exemplary polypeptides disclosed herein. It is appreciated that changes in conserved amino acid bases between NOXA1 (synonymously known as p51$^{nox}$) and p67$^{phox}$ are most likely to impact the activity of the resultant molecule (21). As the present invention is intended to lessen relative activity through competitive binding relative to wild-type species of NOXA1 (SEQ ID NO: 1)or p67$^{phox}$(SEQ ID NO: 5), changes in such regions are recognized to decrease the rate of complexation by gp91$^{phox}$ and other cytosolic cofactors and thereby reduced superoxide production, however such changes in the extreme case of excess length and/or hydropathic index can reduce competitive effectiveness relative to wild-type species. Certain amino acid substitutions for other amino acids in a sequence are known to occur without appreciable loss of activity.

In making such changes, the hydropathic index of amino acids are considered. According to the present invention, certain amino acids can be substituted for other amino acids having a similar hydropathic index and still result in a polypeptide with similar biological activity. Each amino acid is assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine −3.5); aspartate (−3.5); asparagine (−3.5); lysine (−3.9); and arginine (−4.5).

Without intending to be limited to a particular theory, it is believed that the relative hydropathic character of the amino acid determines the secondary structure of the resultant polypeptide which in turn defines the interaction of the polypeptide with other molecules. It is known in the art that an amino acid can be substituted by another amino acid having a similar hydropathic index and still obtain a functionally equivalent polypeptide with the exception of the critical SH3 domain tryptophan residue found at residues 436 and 494 of wild-type NOXA1 and p67$^{phox}$ respectively. In such changes, the substitution of amino acids whose hydropathic indices are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

An inventive NOXA1 or p67$^{phox}$ mutant nucleotide sequence can be composed of any polyribonucleotide or polydeoxribonucleotide. By way of example, an inventive NOXA1 or p67$^{phox}$ nucleotide sequence is composed of single- and double-stranded DNA, DNA that is a mixture of single- and double-stranded regions, single- and double-stranded RNA, and RNA that is mixture of single- and double-stranded regions, hybrid molecules including DNA and RNA that are single-stranded or, more typically, double-stranded, or a mixture of single- and double-stranded regions. In addition, the inventive NOXA1 or p67$^{phox}$ nucleotide sequence are optionally composed of triple-stranded regions including RNA, or DNA, or both RNA and DNA. An inventive NOXA1 or p67$^{phox}$ nucleotide sequence optionally also contains one or more modified bases or DNA or RNA backbones modified for stability or for other reasons. "Modified" bases illustratively include tritylated bases and inosine.

An inventive polypeptide is composed of amino acids joined to each other by peptide bonds, or modified peptide bonds, such as peptide isosteres, and optionally contain amino acids other than the 20 gene-encoded amino acids. An inventive polypeptide may be modified by either natural processes, such as posttranslational processing, or by chemical modification techniques which are well known in the art. Such modifications are well described in basic texts and in more detailed monographs, as well as in a voluminous research literature. Modifications can occur anywhere in an inventive polypeptide, including the peptide backbone, the amino acid side-chains and the amino or carboxyl termnini. It will be appreciated that the same type of modification may be present in the same, or varying degrees at several sites in a given inventive polypeptide. Also, a given inventive polypeptide optionally contains many types of modifications illustrative including acetylation, acylation, ADP-ribosylation, amidation covalent attachment of flavin, covalent attachment of a heme moiety, covalent attachment of a nucleotide or nucleotide derivative, covalent attachment of a lipid or lipid derivative, covalent attachment of phosphotidyhnositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (21-24).

Inventive NOXA1 and p67$^{phox}$ mutants having diminished relative activity compared to wild-type NOXA1 (SEQ ID NO: 1) and p67$^{phox}$(SEQ ID NO: 5), respectively are generated through the insertion of an at least 3 amino acid insert having a hydropathic index of between −2.4 and 1.6 into the C-terminal SH3 domain between conservative motifs PEDL (SEQ ID NO: 35) (415-418 NOXA1, 473-476 p67$^{phox}$) and GIFPK (SEQ ID NO: 34) (446-450 NOXA1, 504-508 p67$^{phox}$).The point of adjacent exons intersection is appreciated to be a particularly convenient locale for an insertion. In NOXA1 the joiner between exons 13 and 14 occurs between amino acid residues 430 and 431. More preferably, the insert is from 4 to 12 bases in length. The hydropathic index of the insert is preferably between −2.4 and 1.6 and more preferably between −1.4 and 0.6. Relative activity of an inventive mutant is further diminished relative to the wild-type by excision-, addition-, or deletion-mutation within the activation domain of NOXA1 polypeptide (bases 200-214 of SEQ ID NO. 1) or p67$^{phox}$ polypeptide (bases 199-213 of SEQ ID NO. 5). Alternatively, or in combination with activation domain mutation, point mutations within the C-terminus SH3 domain are also accomplished to diminish relative activity. The tryptophan residue of the C-terminus SH3 domain is a particularly preferred situs for a point mutation, preferably to a residue of extreme hydropathic index value of greater than an absolute value of 1.9. It is appreciated that a chimera of NOXA1 and p67$^{phox}$ incorporating the above-described insert mutant is also operative as a therapeutic to diminish ROS production by NOX species NOX1-4.

Mutagenesis can be performed utilizing any one of several techniques known to those of skill in the art. For example, a particular mutagenesis protocol is followed utilizing the Quikchange Site-Directed Mutagenesis Kit from Stratagene (La Jolla, Calif.). This procedure requires the use of two complementary synthetic oligonucleotide primers, each encoding the intended nucleotide change, with length and sequence also dictated by the nucleotides flanking the change site according to parameters described in the kit manual, Double-stranded plasmid DNA, comprising the DNA sequence to be mutagenized/changed, serves as the mutagenesis template. The mixed primers are annealed to heat denatured template DNA and extended using free deoxy-nucleotides and the thermostable high-fidelity Pfu DNA polymerase. Multiple rounds of heat denaturation, annealing and extension are performed in a thermocycler to produce adequate quantities of linear single-stranded plasmid representing each complementary strand of the plasmid template. As each de novo strand arises from the extended mutagenesis primer, it also contains the intended nucleotide change. As the complementary strands anneal, the primary product is double-stranded plasmid, circularized by annealing through the overlap provided by the complementary primers. To eliminate the residual template DNA, the product is digested with restriction endonuclease Dpn I which selectively cleaves DNA that has been modified by in vivo methylation at its recognition site; because the in vitro synthesized mutagenesis product is not methylated, it survives the treatment with Dpn I. The newly synthesized, annealed, circularized and Dpn I digested plasmid DNA containing the nucleotide change is used to transform competent E. coli cells. Cell colonies arising from this transformation are screened by DNA sequence analysis to verify their containing the mutant sequence.

In a variation of the Quikchange procedure as described in the kit manual, the following changes can be made. The nucleotides, buffers and enzymes used may, or may not, be components of the commercially available kit. The reaction mix contains 300 nM of each primer. After the recommended number of cycles in the thermocycler, the reaction mix is checked by electrophoresis of a small aliquot through a 0.8-1.0% agarose gel to confirm the existence of de novo plasmid DNA. Following digestion with Dpn I, excess primer is removed by purification of the plasmid DNA using the QIAquick PCR Purification Kit from Qiagen (Valencia, Calif.). The purified DNA is then heated to remove any residual primer from the linear plasmid ends, and then cooled to allow annealing of the complementary ends before transformation of the E. coli cells.

Mutagenesis can also be performed as described in Maniatis, et al. (47). In an example of such a procedure, the wild-type NOXA1 or p67$^{phox}$ nucleotide sequence is subcloned into a bacteriophage M13 vector and single-stranded DNA is prepared as described by Maniatis. An oligonucleotide primer is designed for each mutation. The olgonucleotide primer has the same sequence as a portion of the wild-type sequence except at the site of the desired mutation where one or two nucleotides are substituted for the wild-type nucleotides. The length of the oligonucleotide primer depends on the exact sequence in the area of the desired mutation and is determined as described in Maniatis. The mutagenic oligonucleotide primer is phosphorylated with T4 polynucleotide kinase by mixing 100-200 pmoles of the mutagenic oligonucleotide with 2 microliters of 10×bacteriophage T4 polynucleotide kinase buffer, 1 microliter of a 10 millimolar solution of ATP, 4 units of bacteriophage T4 polynucleotide kinase and water to a total reaction volume of 16.5 microliters. The 10×bacteriophage T4 polynucleotide kinase buffer is composed of 0.5 M Tris.Cl (pH 7.6), 0.1 M MgCl$_2$, 50 millimolar dithiothreitol, 1 millimolar spermidine HCl and 1 millimolar EDTA. The reaction is incubated for 1 hour at 37° C. and then heated at 68° C. for 10 minutes. The mutagenic oligonucleotide primer is annealed to single-stranded DNA in a mixture of 0.5 pmole single-stranded DNA, 10 pmoles phosphorylated mutagenic oligonucleotide, 10 pmoles non-phosphorylated universal sequencing primer complementary to a region of the vector, 1 microliter of 10×PE1 buffer and water to a total reaction volume of 10 microliters. The 10×PE1 buffer is composed of 200 millimolar Tris base, pH 7.5, 500 millimolar NaCl, 100 millimolar MgCl$_2$ and 10 millimolar dithiothreitol. The mixture is heated to a temperature 20° C. above the theoretical T$_m$ of a perfect hybrid formed between the mutagenic oligonucleotide for 5 minutes. The theoretical T$_m$ is calculated from the formula Tm=4(G+C)+2 (A+T). The mixture is allowed to cool to room temperature over a period of about 20 minutes. Primer extension and ligation are performed by mixing 1 microliter of 10×extension buffer (which is composed of 200 millimolar Tris base, pH 7.5, 100 millimolar MgCl$_2$, 100 millimolar dithiothreitol), 1 microliter of 10 millimolar ATP, water to 8.5 microliters, 1 microliter of a solution of the four dNTPs (dGTP, DATP, dTTP, and dCTP), each at a concentration of 2 millimolar, 5 Weiss units of T4 DNA ligase and 2.5 units of Klenow fragment of E. coli DNA polymerase I. Ten microliters of the primer extension/ligation mixture are added to the single-stranded DNA/oligonucleotide mixture. The reaction is then incubated at 16° C. for 6-15 hours.

The reaction mixture is then used to transform E. coli of an appropriate strain and plaques are screened by hybridization with an appropriate labeled probe, e.g. the mutagenic oligonucleotide primer.

Another exemplary inventive insert mutant includes the insertion of a polypeptide fragment of a Lys-Ile-Thr tripeptide in place of Glu-Pro-Asp-Val-Pro-Leu-Ala in NOXA1$_{inhib}$ (SEQ ID NO. 2). Table 1 lists a variety of mutants according to the present invention with corresponding homologous mutants for NOXA1 and p67$^{phox}$.

of the critical tryptophan residue in the SH3 domain of the wild-type NOXA1 or p67$^{phox}$ did not inhibit oxidase activity

TABLE 1

Exemplary Inventive Mutants Relative to Wild-Type NOXA1 (SEQ ID NO. 1) and p67$^{phox}$ (SEQ ID NO. 5)

| Designation | Wild-Type | Residue Within Sequence and Insert | Deletion Wild-Type Residues | Point Mutations | Approx. Relative Activity (100% Wild-Type) |
|---|---|---|---|---|---|
| NOXA1$_c$ W436R | NOXA1 | 431-Pro-His-Val-Gly-Ala SEQ ID NO. 6 | 200-214 activation domain | W436R | 0 |
| NOXA1$_d$ | NOXA1 | 438-Glu-Pro-Asp-Val-Pro-Leu-Ala SEQ ID NO. 7 | — | — | ~15 |
| NOXA1$_e$ | NOXA1 | 418-Phe-Val-Pro-Val-Asp-Ser-Lys-Glu-Arg-His SEQ ID NO. 8 | — | R327C | ~2 |
| NOXA1 W436R | NOXA1 | — | — | W436R | ~21 |
| NOXA1$_{(SH3+)}$ C320R | NOXA1 | 431-Glu-Pro-Asp-Val-Pro-Leu-Ala SEQ ID NO. 7 | — | C320R | ~2 |
| NOXA1$_{(SH3+)}$ | NOXA1 | 431-Glu-Pro-Asp-Val-Pro-Leu-Ala SEQ ID NO. 7 | — | — | ~13 |
| p67$^{phox}$$_{inhib}$ | p67$^{phox}$ | 488-Glu-Pro-Asp-Val-Pro-Leu-Ala SEQ ID NO. 7 | — | V209R | 0 |
| p67$^{phox}$$_c$ W_R | p67$^{phox}$ | 488-Pro-His-Val-Gly-Ala SEQ ID NO. 6 | 199-213 activation domain | W494R | 0 |
| p67$^{phox}$$_d$ | p67$^{phox}$ | 495-Glu-Pro-Asp-Val-Pro-Leu-Ala SEQ ID NO. 7 | — | — | ~15 |
| p67$^{phox}$$_e$ | p67$^{phox}$ | 476-Phe-Val-Pro-Val-Asp-Ser-Lys-Glu-Arg-His SEQ ID NO. 8 | — | Y372I | ~5 |
| p67$^{phox}$ W436R | p67$^{phox}$ | — | — | W494R | ~25 |
| p67$^{phox}$$_{(SH3+)}$ C320R | p67$^{phox}$ | 495-Glu-Pro-Asp-Val-Pro-Leu-Ala SEQ ID NO. 7 | — | Y358I | ~2 |
| p67$^{phox}$$_{(SH3+)}$ | p67$^{phox}$ | 488-Glu-Pro-Asp-Val-Pro-Leu-Ala SEQ ID NO. 7 | — | — | ~17 |

A second inventive NOXA1 or p67$^{phox}$ variant that lacked the activation sequence, but included an extra nucleotide sequence insert in the C-terminal SH3 domain was NOXA1$_{inhib}$ and p67$^{phox}$$_{inhib}$ respectively. These variants included the insertion of an extra peptide, EPDVPLA, into the SH3 domain of the protein intermediate between PEDL (SEQ ID NO: 35) and GIFPK (SEQ ID NO: 34) conservative motifs of the wild-type proteins. Since NOXA1$_{inhib}$ and p67$^{phox}$$_{inhib}$ are not active due to the absence of the activation domain, the influence of the extra peptide on function is determined by insertion mutation between PEDL (SEQ ID NO: 35) and GIFPK (SEQ ID NO: 34) conservative motifs of the wild-type proteins with an intact wild-type activation domain. This reduced the activity of the wild-type protein by ~90%. Point mutation within the activation domain is observed to limit activity of the resulting mutant to a degree dependent on the hydropathic index of the base residue and substitute, as well as the role a particular residue plays in binding, as evidenced by p67$^{phox}$$_e$ of Table 1. Inventive proteins containing insertion mutations and intact activation domains functioned as dose-dependent, transdominant inhibitors of the truncated versions of NOXA1 (SEQ ID NO. 1 residues 1-273+Ala51Thr, Thr261Ala) and p67$^{phox}$ (SEQ ID NO: 5 residues 1-224) and wild-type NOXA1 (SEQ ID NO. 1) and p67$^{phox}$ (SEQ ID NO. 5), inhibiting activities by as much as 80%. This inhibition is specific in the case of NOXA1$_{inhib}$ is effective in inhibiting the NOX1/NOXO1/NOXA1 oxidase system in reconstituted K562 cells.

The presence of the SH3 domain peptide insert reduced or eliminated the binding of the inventive cytosolic cofactor SH3 domain to the C-terminal region of NOXO1 or p47$^{phox}$. The deletion and mutation studies detailed herein indicate a lack of function of NOXA1$_{(SH3+)}$ or p67$^{phox}$$_{(SH3+)}$. Mutation to the same degree as observed with the peptide insertion as shown in exemplary FIG. 6. An alternatively spliced product of the src gene, which is expressed in neuronal tissues, encodes a protein (N-src) with a hexapeptide insertion in the SH3 domain similar in location to the insertion in NOXA1$_{(SH3+)}$ (25).

Inventive polypeptides or nucleic acids are provided as a therapeutic to reduce reactive oxygen species production through competitive binding relative to wild-type cytosolic co-factors NOXA1 and/or p67$^{phox}$ within a subject.

Nucleic Acid Sequence Administration

An inventive nucleic acid sequence encoding an insert mutant of NOXA1 and/or p67$^{phox}$, optionally containing other deletion, insertion or point mutations, is administered to treat, inhibit or prevent a disease or disorder associated with aberrant expression and/or activity of a NOX species NOX1, NOX2, NOX3, or NOX4, by way of gene therapy. Gene therapy refers to therapy performed by the administration to a subject of an expressed or expressible nucleic acid. In this embodiment of the invention, the nucleic acid sequence produces the encoded protein that mediates a therapeutic effect.

Any of the methods for gene therapy available in the art can be used according to the present invention. Exemplary methods are described below.

For general reviews of the methods of gene therapy (26-28). Preferably, the compound includes nucleic acid sequences encoding an inventive mutant and immune response suppressive RNA, the nucleic acid sequences being part of an expression vector that expresses the inventive mutant in a suitable host cell. In particular, such nucleic acid sequence has a promoter operably linked to the NOXA1 and/or p67$^{phox}$ mutant coding region. It is appreciated that the promoter is either inducible or constitutive, and, optionally, tissue-specific. In another particular embodiment, nucleic acid molecules are used in which the mutant coding sequences and any other desired sequences are flanked by regions that promote homologous recombination at a desired site in the genome, thus providing for intrachromosomal expression of the NOXA1and/or p67$^{phox}$ mutant encoding nucleic acids (30, 31).

Delivery of the nucleic acids into a subject may be either direct, in which case the subject is directly exposed to the nucleic acid sequence or nucleic acid sequence-containing vector, or indirect, in which case, cells are first transformed with the nucleic acids in vitro, then transplanted into the subject. These two approaches are known, respectively, as in vivo or ex vivo gene therapy.

The inventive nucleic acid sequence is optionally directly administered in vivo, where the sequence is expressed to produce the encoded polypeptide. This can be accomplished by conventional methods known in the art, such as by constructing the sequence as part of an appropriate nucleic acid expression vector and administering the sequence so that the sequence becomes intracellular. This is accomplished for example by infection using defective or attenuated retrovirals or other viral vectors (31), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (32).

Alternatively, a nucleic acid sequence complex with a ligand is formed in which the ligand has a fusogenic viral peptide to disrupt endosomes, thereby allowing the nucleic acid sequence to avoid lysosomal degradation. Additionally, the nucleic acid sequence is targeted in vivo for cell specific uptake and expression, by targeting a specific receptor (33-37). Alternatively, the nucleic acid is introduced intracellularly and incorporated within host cell DNA for expression, by homologous recombination (29, 30).

In a specific embodiment, viral vectors that contain nucleic acid sequences encoding an inventive mutant are used. For example, a retroviral vector can be used. These retroviral vectors contain the components necessary for the correct packaging of the viral genome and integration into the host cell DNA. The nucleic acid sequences encoding the inventive NOXA1 or p67$^{phox}$ mutant to be used in gene therapy are cloned into one or more vectors that facilitate delivery of the gene into a subject (26-28).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Techniques are conventional to the art for the introduction of foreign genes into cells (38) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells such as hematopoietic stem or progenitor cells are preferably administered intravenously. The amount of cells envisioned for use depends on factors including in part the desired effect, patient state, disease state, and can be determined by one skilled in the art.

Cells into which a nucleic acid can be introduced for purposes of gene therapy encompass any desired available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, and fetal liver. Preferably, the cell used for gene therapy is autologous to the patient.

In an embodiment in which recombinant cells are used in gene therapy, nucleic acid sequences encoding an inventive NOXA1 or p67$^{phox}$ mutant are introduced into the cells such that they are expressible by the cells or their progeny, and the recombinant cells are then administered in vivo for therapeutic effect. In a specific embodiment, stem or progenitor cells are used. Any stem and/or progenitor cells which are isolatable and maintained in vitro can potentially be used in accordance with this embodiment of the present invention.

In a specific embodiment, the nucleic acid to be introduced for purposes of gene therapy includes an inducible promoter operably linked to the coding region, such that expression of the nucleic acid is controllable by controlling the presence or absence of the appropriate inducer of transcription.

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include the effect of a compound on a cell line or a patient tissue sample. The effect of the compound or composition on the cell line and/or tissue sample can be determined utilizing techniques known to those of skill in the art including, but not limited to, superoxide formation assays, immunoblotting, and competitive binding assays.

The invention provides methods of treatment, inhibition or prophylaxis by administration to a subject of an effective amount of an inventive NOXA1 or p67$^{phox}$ mutant or pharmaceutical composition of the invention. Preferably, the inventive mutant polypeptide is purified to eliminate side-effects. A subject according to the present invention is a non-human animal such as a cow, pig, horse, chicken, cat, dog, mouse, rat, monkey, and rabbit; and a human.

An inventive polypeptide is preferably modified for in vivo administration with a membrane-permeable arginine-rich peptide for transmembrane delivery to subject cells. Similarly, pentratin or transportan is attached to or incorporated within any ligand portion of the NOXA1 or p67$^{phox}$, mutant with the proviso that PB1, SH3 portions of the mutant are maintained. Preferably, such membrane permeable moieties are added to the 5' terminal of the mutant. In each situation, the mutant containing the membrane-permeable arginine-rich peptide, pentratin, or transportan serves to carry the NOXA1 or p67$^{phox}$ into the targeted cell.

Arginine-rich peptides which are internalized after contact with the cell membrane have been shown to transport covalently coupled proteins into cells (39-40). Examples of such internalization moieties illustratively include: membrane-permeable arginine-rich peptides, pentratin, transportan and its deletion analogs.

```
GRKKRRQRRRPPQ           (SEQ ID NO. 9)
                        (TAT 48-60)

GRRRRRRRRRPPQ           (SEQ ID NO. 10)
                        (R9-TAT)

TRQARRNRRRRWRERQR       (SEQ ID NO. 11)
                        (HIV-1 Rev 34-50)

RRRRNRTRRNRRRVR         (SEQ ID NO. 12)
                        (FHV coat 35-49)

KMTRAQRRAAARRNRWTAR     (SEQ ID NO. 13)
                        (BMV gag 7-25)

TRRQRTRRARRNR           (SEQ ID NO. 14)
                        (HTLV-II Rex 4-16)
```

Other membrane-permeable peptides are pentratin and transportan,

```
                                        (SEQ ID NO. 15)
RQIKIWFQNRRMKWKK
(Atennapedia 43-58 - pentratin)

(SEQ ID NO. 16)
LIKKALAALAKLNIKLLYGASNLTWG
(transportan) (Muratovska and Eccles 2004)
```

(SEQ ID NO. 16).

Alternative amino acid composition for transportan and its deletion analogs which maintain membrane transduction properties (Soomets et al. 2000):

```
                                (SEQ ID NO. 17)
GWTLNSAGYLLGKINLKALAALALKKIL    (transportan)

(SEQ ID NO. 18)
LNSAGYLLGKINLKALAALAKKIL        (transportan 7)

(SEQ ID NO. 19)
GWTLNSAGYLLGKLKALAALAKKIL       (transportan 9)

(SEQ ID NO. 20)
AGYLLGKINLKALAALAKKIL           (transportan 10)

(SEQ ID NO. 21)
LNSAGYLLGKLKALAALAKKIL          (transportan 12)

(SEQ ID NO. 22)
AGYLLGKLKALAALAKKIL             (transportan 14)
```

Various delivery systems are known and are optionally used to administer a compound of the invention. These systems illustratively include encapsulation in -liposomes, -microparticles, -microcapsules, recombinant cells capable of expressing the compound, receptor-mediated endocytosis, and construction of a nucleic acid as part of a retroviral or other vector. Routes of introduction illustratively include intradermal, intramuscular, intraperitoneal, intravenous, subcutaneous, intranasal, epidural, and oral. The inventive nucleic acid or polypeptides or compositions thereof are administered by specific routes illustratively including infusion or bolus injection, absorption through epithelial or mucosal linings, and administration together with other biologically active agents. The inventive nucleic acid or polypeptides or compositions thereof are administered into the central nervous system by a route illustratively including intraventricular injection and intrathecal injection. Intraventricular injection is optionally via intraventricular catheter, as might be attached to an Omaya reservoir.

In a specific embodiment, it may be desirable to administer the pharmaceutical compounds or compositions of the invention locally to the area in need of treatment; this may be achieved by routes illustratively including local infusion during surgery, topical application, by injection, via a catheter, via a suppository, or via an implant.

The inventive nucleic acid or polypeptides or compositions thereof are optionally administered in a vesicle, in particular a liposome (41). Controlled release delivery systems conventional to the art are also operative herein.

The term "pharmaceutically acceptable" is intended to mean approved by a regulatory agency of the federal or a state government or listed in the U.S. Pharmacopoeia or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pins, capsules, powders, sustained-release formulations and the like. The composition can be formulated as a suppository, with traditional binders and carriers such as triglycerides. Oral formulation illustratively include standard carriers such as pharmaceutical grades of mannitol, lactose, starch, magnesium stearate, sodium saccharine, cellulose, and magnesium carbonate (42). Such compositions contain a therapeutically effective amount of the inventive mutant, preferably in purified form, together with a suitable amount of carrier so as to provide the form for proper administration to the subject.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts have previously been defined.

The amount of the compound of the invention which will be effective in the treatment, inhibition and prevention of a disease or disorder associated with excessive reactive oxygen species production is established by standard clinical techniques. In addition, in vitro assays may optionally be employed to help identify optimal dosage ranges. The precise dose to be employed in the formulation also depends on the route of administration, and the seriousness of the disease or disorder, and should be decided according to the judgment of the practitioner and each subject's circumstances. Effective doses may be extrapolated from dose-response curves derived from in vitro or animal model test systems.

For polypeptides, the dosage administered to a subject is typically 0.1 mg/kg to 100 mg/kg of the patient's body weight. Preferably, the dosage administered to a subject is between 0.1 mg/kg and 20 mg/kg of subject body weight, more preferably 1 mg/kg to 10 mg/kg of subject body weight. Dosage and frequency of administration of inventive polypeptides are reduced by enhancing uptake and membrane penetration.

The present invention also provides a pharmaceutical pack or kit containing one or more containers filled with one or more of the ingredients of the pharmaceutical compositions of the invention. Optionally associated with such a container are instructions for administration and dosing commensurate with the route of administration and subject characteristics.

The present invention is further illustrated with respect to the following non-limiting examples principally pertaining to the exemplary inventive mutant designates NOXA1$_{inhib}$ and NOXA1$_{(SH3+)}$. It should be appreciated that comparable results are obtainable for other NOXA1 and p67$^{phox}$ mutants.

EXAMPLE 1

Plasmids

The cDNA for human NOX1 and NOXO1 in pcDNA 3.1/neo are gifts from Botond Banfi, University of Geneva. An upstream NheI site and Kozak sequence are introduced into the NOX1 cDNA by site-directed mutagenesis and then it is subcloned back into pcDNA3.1/Neo(+). NOXO1 cDNA is subcloned into pcDNA3.1/Zeo(-) (Invitrogen, Carlsbad, Calif.). Human NOXA1 in pEF-BOS is a gift from Hideki Sumimoto, Kyushu University (19). The NOXA1 cDNA is excised from pEF-DOS with BamHI and EcoRI and cloned into the corresponding sites of pGEM-3Zf(+). The cDNA is then cut from this vector with XbaI and EcoRI and subcloned into the NheI and EcoRI sites of pCI-neo (Promega, Madison, Wis.). Orientation and sequence of each construct is confirmed by nucleotide sequencing (Advanced Nucleic Acids Core Facility, UTHSCSA). The cDNAs for human p67$^{phox}$ and p47$^{phox}$ are subcloned into pCI-neo and pcDNA3.1/Zeo (-). Site-directed mutagenesis is carried out using the QuikChange kit (Stratagene, La Jolla, Calif.).

EXAMPLE 2

CaCo2 Cell Culture and NOXA1 Variant cDNA Preparation

CaCo2 colon carcinoma cells are cultured in DMEM supplemented with 10% fetal bovine serum (FBS) and 100 Units/milliliter (U/ml) of penicillin and 100 μg/ml streptomycin (P/S), and passaged when confluent. Total cell RNA is isolated from either confluent cells, either untreated or incubated for 48 h in complete medium containing 5 mM sodium butyrate. RNA isolation is carried using the TRIzol® reagent (Invitrogen), and the RNA pellets are solubilized in nuclease-free H$_2$O. Reverse transcription of 2 μg RNA is carried out using random decamers and MMLV reverse transcriptase following the manufacturer's protocol (RETROscript kit, Ambion Inc., Austin, Tex.). NOXA1 cDNAs are prepared from the reverse-transcribed RNA by two rounds of polymerase chain reaction, using the nested human NOXA1 primer pairs, sense primer 1: 5'-CCG GCC CCT CCG CGG GAT CCT-3' (SEQ ID NO. 23); anti-sense primer 1: 5'-TTA AAA GCA TCA TGG ACA CAG CA-3' (SEQ ID NO. 24); and sense primer 2: 5'-GGG ATC CTG GCC CCT CCT CGA-3' (SEQ ID NO. 25); anti-sense primer 2: 5'-GAC ACA GCA TCA TTA GGG CTG A-3' (SEQ ID NO. 26), and the enzyme Platinum Taq DNA polymerase High Fidelity (Invitrogen). The PCR products are cloned into pCRII-TOPO (Invitrogen), and nucleotide sequencing carried out on the inserts from several recombinant clones.

EXAMPLE 3

Fusion Proteins and Antibody Preparation

An EcoRI fragment of NOXO1 (encoding residues 39-370) is cloned in-frame with the maltose-binding protein (MBP) in pMAL-c2X (New England Biolabs, Boston, Mass.). For NOXA1, an EcoRI site is inserted 5' to the translation initiation codon of NOXA1$_{trunc}$ cDNA by PCR amplification and this construct cloned in-frame with glutathione-S-transferase in the baculovirus transfer vector pAcG3X (PharMingen, San Diego, Calif.). Recombinant baculovirus expressing GST-NOXA1$_{trunc}$ is prepared in Sf9 cells using standard procedures. For NOX1, cDNA encoding residues 124-167 is prepared by PCR amplification with a SacI site at the 5' end and a stop codon and HindIII site at the 3' end. This is inserted in-frame with MBP at the corresponding sites of the vector pET23bMBPH6 (43). MBP fusion proteins are induced and purified on amylose resin (New England Biolabs) using standard procedures. GST-NOXA1$_{trunc}$ is isolated from the lysate of Sf9 cells infected 72 h previously with the recombinant baculovirus. GST-NOXA1$_{trunc}$ is purified on GSH-Sepharose 4B (Amersham Biosciences Corp, Piscataway, N.J.) using standard procedures. Antibodies are prepared in rabbits using protocols approved by the Institutional Animal Care and Use Committee.

For the protein interaction studies, the complete coding sequences of NOXA1 and NOXA1$_{(SH3+)}$ are first prepared by PCR amplification of the parent plasmids, using the sense primer 5'-CCC GGG ATG GCC TCT CTG GGG GAC CT-3' (SEQ ID NO. 27) and the anti-sense primer 5'-CCC GGG TTA GGC CTG ATC TCC CTG CTG-3' (SEQ ID NO. 28). This resulted in cDNAs with XmaI restriction sites at the 5' and 3' ends. The cDNA products are cloned into the pCRII- TOPO vector (Invitrogen), excised with XmaI and subcloned into the XmaI site of the vector pGEX-3X, in-frame with GST sequence.

The cDNA encoding fusion proteins of GST and the SH3-containing C-terminal ends of NOXA1 (Gly386 to Pro476) and NOXA1$_{(SH3+)}$ (Gly386 to Pro483) are prepared by PCR as above, using the sense primer 5'-GAA TTC CGG GGG TCG GCC GGT CCT-3' (SEQ ID NO. 29) and the anti-sense primer 5'-CCC GCG TTA GGG CTC ATC TCC CTG CTG-3' (SEQ ID NO. 30). The products are cloned into pCRII-TOPO, excised with EcoRI, and cloned in-frame with GST into the EcoRI site of pGEX-3X. Fusion proteins are induced and bacterial cell lysates prepared using standard procedures.

To prepare MBP-NOXO1$_{(288-370)}$ for the binding assays, cDNA for the C-terminal end of NOXO1 (encoding residues Glu288 to Gln370) is prepared by amplification of the NOXO1/pcDNA3.1 plasmid using a mutant sense primer 5'-GTG CTG CTg agc tcG GAA GGG CTG GGC GCT-3' (SEQ ID NO. 31) (which introduces a SacI site—lower case) and the anti-sense primer 5'-TAG AAG GCA CAG TCG AGG CT-3' (SEQ ID NO. 32) (the BGH site in pcDNA3.1). The PCR product is digested with SacI and XhoI and cloned into the same sites in the vector pET23bMBPH6 in-frame with the maltose binding protein (MBP).

EXAMPLE 4

Stable Expression of NOX2, NOX1, and NOXO1 in K562 Cells

K562 cells grown in complete RPMI medium (RPMI-1640 with 10% FBS and P/S) are washed and resuspended to 15×10$^6$ cells/ml in complete medium. Linearized cDNA for NOXO1 in pcDNA3.1/Zeo(−) (25 μg in 15 μl H$_2$O) is added to 375 μl of the cells and a 325 μl aliquot electroporated at 250 V/960 μFd. Stable expressing cells are selected in 250 μg/ml zeocin for 14 days. Single cell clones are established by limiting dilution in 96-well plates. Expression of NOXO1 in the selected clones is determined by immunoblotting of the cell lysates using the antibody to NOXO1 described above.

Human NOX1/pcDNA3.1/Neo(+) plasmid is linearized and transfected into one of the stable K562/NOXO1 clonal cell lines. After selection in 800 μg/ml G418 for 14 days, single cell clones are established by limiting dilution. Since at the time of screening for NOX1expression, a suitable antibody to NOX1 was not available, the clones are tested for phorbol-inducible superoxide activity after transiently expressing NOXA1. Two out of the first twelve clones tested showed significant superoxide production; one of these, K562/NOX1/NOXO1, is used in these studies. The overexpression of NOX1 is later confirmed by immunoblotting with the rabbit antibody MBP-NOX1$_{(124-167)}$. The stable clone of K562 cells expressing human NOX2 (K562/NOX2) has been described previously (24).

EXAMPLE 5

Transient Transfection and Superoxide Assay

The activity of NOXA1 and the NOXA1 variants is determined by transient expression in the K562/NOX1/NOXO1 cell line, and phorbol myristate acetate (PMA, Sigma, St Louis Mo.) stimulated superoxide generation determined using the luminol-based chemiluminescent reagent Diogenes® (National Diagnostics, Atlanta, Ga.). Product specificity is demonstrated by the inhibitory effect of superoxide dismutase (SOD from bovine erythrocytes, S2515, Sigma).

Inhibition by 10 μM diphenylene iodonium chloride (DPI, Sigma D2926) is considered to be evidence for NOX participation. NOXA1 and variant cDNA are cloned into the expression vector pCI-neo (Promega). The NOXA1 plasmids (20 μg) are transfected into ~12×10$^6$ K562/NOX1/NOXO1 cells in 325 μl complete medium by electroporation (250 V/960 μFd). Following 48 h incubation in complete medium supplemented with 10 mM HEPES, the cells are washed twice in Krebs-Ringer solution supplemented with 10 mM glucose (KRG), the viability determined by Trypan blue dye exclusion, and then resuspended in KRG to 6.67×10$^6$ live cells/ml. For the assay, 75 μl (5×10$^5$ live cells) are mixed with 100 μl of the Diogenes® reagent and incubated in a water bath at 37° C. for 5-10 min to equilibrate the cells and to reduce to baseline the chemiluminescence generated following the addition of the cells to the reagent. A 25 μl aliquot of an 8 μg/ml solution of PMA in KRG is then added to the cells and chemiluminescence measured every 2 min for 10 min using a 10 sec integration time in a Turner Designs 20/20 luminometer. Data collected at each time point are corrected by subtraction of zero-time values and are plotted either as arbitrary chemiluminescence units or as a percent of the 10-min chemiluminescence values. For inhibition studies, the corrected chemiluminescence values are plotted versus time and the area under the 10-min curve calculated (SigmaPlot 8.0.2, SSPS Inc, Chicago, Ill.). The transfection and assay of the K562/NOX2 cell line are carried out essentially as described above. To detect the expressed proteins in the transiently transfected cells, 2×10$^6$ live cells in KRG are centrifuged briefly and the pellet heated at 95° C. for 10 min in 100 μl 1 X SDS treatment buffer (90 mM Tris-HCl, pH 8.0, 3.5% SDS, 7.5% 2-mercaptoethanol, 7.5% glycerol).

EXAMPLE 6

Immunoblotting

For the detection of NOXA1 and NOXO1 in transfected K562 cells, 2×10$^6$ live transfected cells are lysed by heating in 100 μl 1×SDS treatment buffer at 95° C. for 20 min, and up to 25 μl separated on 9% SDS-PAGE gels. After transfer to nitrocellulose, the blot is probed with rabbit antiserum to either GST-NOXA1$_{trunc}$ (1:4,000) or to the absorbed MBP-NOXO1$_{39-390}$ (1:2,500) and the bound antibody probed with 1:10,000 horseradish peroxidase-labeled goat anti-rabbit IgG (Pierce, Rockford, Ill.), and visualized by chemiluminescence (SuperSignal West Pico Substrate, Pierce). A similar procedure is used for the detection of p47$^{phox}$ and p67$^{phox}$ and, except that the rabbit antiserum B1 (25) is used as the primary antibody. For the detection of NOX1, crude membrane extracts are first prepared. Approximately 5×10$^7$ cells are treated on ice with diisopropyl fluorophosphate and disrupted by nitrogen cavitation as described previously (26). The cell preparations are subsequently centrifuged at 1,000 g to remove nuclei and intact cells, and the remaining particulate fraction in the supernatant pelleted by centrifugation at 120,000 g for 20 min at 4° C. in a Beckman TL-100 ultracentrifuge. The pellet is extracted for 30 min on ice with 1 ml extraction buffer (20 mM Tris-acetate, pH 7.4, 100 mM KCl, 1 mM EDTA, 1 mM DTT, 20% glycerol, 0.1% Triton N101), and again centrifuged at 120,000 g to remove the insoluble material. The protein concentration in the supernatant is determined using the Bradford reagent (Bio-Rad, Hercules, Calif.). An equal volume of 3×SDS treatment buffer is added and the mixture heated at 95° C. for 10 min. Immunoblotting for NOX1 is carried out as above using antiserum to MBP-NOX1$_{(124-167)}$ as the primary antibody.

EXAMPLE 7

GST-NOXA1 Binding Interactions

Binding interactions are carried out between GST, GST-NOXA1, GST-NOXA1$_{SH3+}$, GST-(SH3wt) and GST-(SH3+) fusion proteins immobilized on GSH-Sepharose, and the in vitro synthesized [$^{35}$S]-labeled target proteins. Volumes of fusion protein bacterial lysates, previously determined to give equal loading of the GSH-Sepharose, are mixed for 5 min at room temperature with 250 µl of a 50% suspension of washed GSH-Sepharose in PBS (137 mM NaCl, 2.68 mM KCl, 10 nM Na2HPO4, pH 7.3). The suspension is washed twice and resuspended to 500 µl in PBS with 10 mM DTT. Human NOX1, NOX2, p47$^{phox}$ and MBP-NOXO1$_{(288-370)}$ are synthesized and labeled in vitro with [$^{35}$S]-methionine/[$^{35}$S]-cysteine (Redivue Pro-mix L-[$^{35}$S] labeling mix, Amersham Biosciences, Inc. # AGQ0080) using the TNT® Coupled Reticulocyte Lysate System (Promega) and T7 RNA polymerase. A 24 µl aliquot of the labeling reaction is mixed with 476 µl of the resuspended immobilized GST fusion protein for 15 min at room temperature. The gel pellet is washed 4× with 500 µl of PBS/10 mM DTT/0.05% Triton X-100. The bound proteins are eluted twice from the gel with 500 µl GSH elution buffer (250 mM NaCl, 10 mM GSH, 100 mM Tris-Cl, pH 8.0) for 5 min. 20 µl of 5×SDS denaturing loading buffer are added to 100 µl of each supernatant and heated at 95° C. for 10 min. The gel pellet containing unreleased activity is resuspended in 380 µl PBS/10 mM DTT/0.05% Triton X-100 and 50 µl of the suspension also treated with the 5×SDS loading buffer as above. The entire volume of the denatured samples is separated on 9% SDS-PAGE and analyzed by fluorography. A sample of the original binding gel is analyzed by denaturing SDS-PAGE and Coomassie staining to confirm the loading of the GST proteins.

EXAMPLE 8

Identification of NOXA1 Structural Variants in CaCo2 Cells

Amplification of cDNA prepared from the total RNA of normal and sodium butyrate-treated CaCo2 cells is carried out using nested NOXA1 gene-specific primers. The primers encompassed the translation initiation and termination sites of human NOXA1. The PCR products, which exhibited multiple bands on agarose gel electrophoresis, are cloned and several recombinant clones sequenced. A number of inventive NOXA1 variants are identified, including transcripts with a variable number of internal exons deleted (gene structure derived from the chromosome 9 nucleotide sequence, GenBank # NT_024000). NOXA1$_{trunc}$ isolated from the RNA of butyrate-treated CaCo2 cells (SEQ ID NO. 33), is a material that contains a C to T mutation at nucleotide 820 of the coding sequence, which converted the CAA codon for Gln274 into a termination signal as shown in FIG. 1 and Table 2. This encodes a truncated NOXA1translation product with the putative PB1 and SH3 domains absent. Other nucleotide mutations resulted in the semi-conserved amino acid changes A51T and T261A (Table 1 and FIG. 1A). A second mutant, NOXA1$_{inhib}$ (GenBank # AY927791) (SEQ ID NO. 2) is prepared from the total RNA isolated from untreated CaCo2 cells. This mutant showed deletion of exons 5 and 6, including the putative NOXA1 activation domain, as well as single nucleotide mutations that resulted in the semi-conservative amino acid substitutions A56T, V73L and the non-conservative mutation C320R as shown in Table 1 and FIG. 1. An alternative splice-acceptor site in exon 14, located 21 bp upstream of the acceptor site predicted by the MRNA sequence of the wild-type NOXA1, induced the insertion in-frame of a heptapeptide sequence EPDVPLA (SEQ ID NO. 7) into the SH3 domain of NOXA1$_{inhib}$. This extra peptide sequence of NOXA1 was identified previously (GenBank # BC041594) by the NIH Mammalian Gene Collection Program (44). The SH3 domain of NOXA1 is highly homologous to the C-terminal SH3 of p67$^{phox}$ (18-20), and both bind the C-terminal region of p47$^{phox}$ (19). Recent studies on the structure of the C-terminal SH3 domain of p67$^{phox}$, (45) demonstrated that the sequence $^{483}$IILVLSKVN$^{491}$ forms the β2 strand of the SH3 binding pocket. The homologous sequence in NOXA1, $^{425}$TVDVLCEVD$^{433}$ is interrupted by the additional peptide in NOXA1$_{inhib}$, as shown in FIG. 1. This markedly alters the interaction between the NOXA1 SH3 domain and both p47$^{phox}$ and NOXO1.

TABLE 2

Nucleotide and Amino Acid Differences in NOXA1$_{trunc}$ and NOXA1$_{inhib}$ Compared With Wild-Type NOXA1 (SEQ ID NO. 1)

| NOXA1$_{trunc}$ | | NOXA1$_{inhib}$ | |
|---|---|---|---|
| Nucleotide Change | Amino Acid Change | Nucleotide Change | Amino Acid Change |
| G151A | Ala 51 Thr | G166A | Ala 56 Thr |
| A781G | Thr 261 Ala | T183C | no change |
| C820T | Gln 274 stop | G217C | Val 73 Leu |
| A829G | — | G424C | Ala 142 Thr |
| A912del | — | 505-672del | delete AAs 169-224 |
| T1202C | — | T958C | Cys 320 Arg |
| G1394A | — | G1294 insert AGC CCG ATG TCC CCC TTG CAG | Insert: Glu-Pro-Asp-Val-Pro-Leu-Ala at Glu431 |

EXAMPLE 9

Regulation of NOX1 Activity by NOXA1 and NOXA1$_{trunc}$

Figure 3:
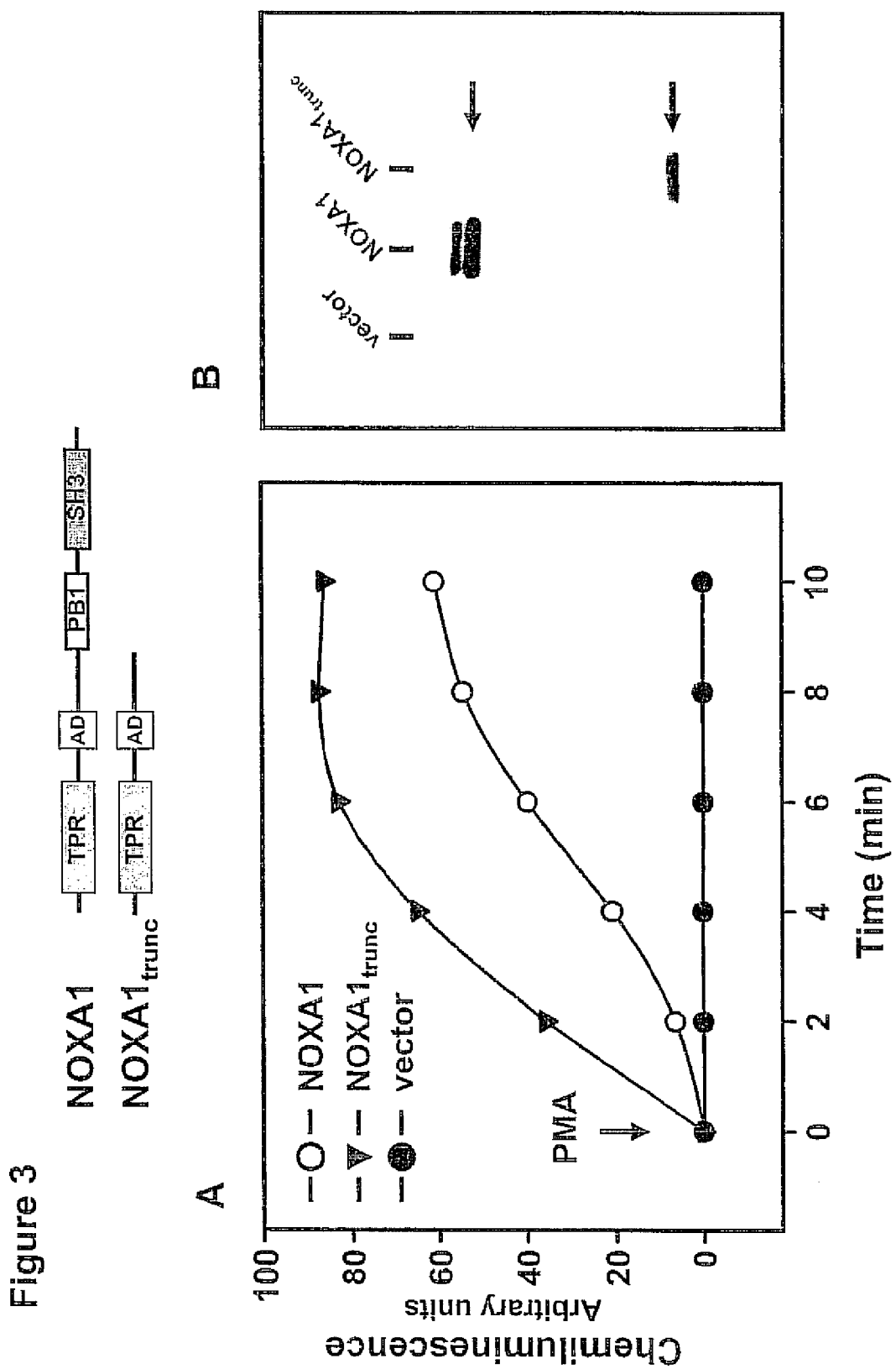
FIG. 3(A) is a plot of chemiluminescence as a function of time showing superoxide production by the K562/NOX1/NOXO1 cell line expressing NOXA1 (SEQ ID NO: 1) and NOXA1$_{trunc}$ (SEQ ID NO: 1 residues 1-273+Ala51Thr, Thr261Ala) and (B) is an electrophoretic immunoblot showing expression levels of NOXA1 and NOXA1$_{trunc}$.

NOXA1and NOXO1 function as cofactors for the NADPH oxidase core enzyme protein NOX1. The functional ability of the NOXA1 variants is studied by transient expression in a K562 cell line that stably expresses both NOX1 and NOXO1, followed by assay of PMA-stimulated superoxide generation. The K562/NOX1/NOXO1 cell line expressed both NOXO1 and NOX1 at levels detectable by immunoblotting, whereas neither is detected in untransfected cells (FIG. 2). For NOXO1 detection, the indicated K562 cells are lysed in SDS-PAGE treatment buffer and 1.5×10$^5$ cell equivalents separated by SDS-PAGE on 9% gels. Immunoblotting is carried out as detailed in Experimental Procedures. For NOX1 detection, SDS-PAGE and immunoblotting are carried out on membrane extracts from approximately 5×10$^6$ of each cell type. The slowly migrating bands indicated by asterisks appear to be non-specific. K562/NOX1/NOXO1 cells transfected with either NOXA1 or NOXA1$_{trunc}$ exhibited production of superoxide. Constitutive, SOD-inhibitable activity is observed immediately after addition of the washed cells to the Diogenes reagent, but this decayed to baseline levels within 3 to 6 min. Addition of PMA (1 µg/ml) at this point resulted in a marked stimulation (40- to 80-fold) of superoxide production, which reached a plateau within 10 min (FIG. 3A). Activity is inhibited by addition of either SOD or DPI (data not shown), and no activity is observed when the cells are transfected with empty vector, indicating that PMA-stimulated production of superoxide in this transfected cell model is mediated almost entirely by the NOX1/NOXO1/NOXA1 NADPH oxidase complex. When expressed at similar levels, the activity of NOXA1$_{trunc}$ is equal to or greater than that seen with the wild-type NOXA1 (SEQ ID NO: 1) (FIG. 3B). Thus, essentially normal levels of NADPH oxidase activity were observed with a NOXA1 variant from which both PB1 and SH3 domains were absent.

The time course of PMA-stimulated superoxide production with NOXA1$_{trunc}$ suggested a more rapid induction and approach to plateau levels than is observed with wild-type NOXA1. To investigate this more closely, multiple transfection experiments are carried out and the data normalized to permit a statistical comparison. Baseline chemiluminescence values obtained at zero time were subtracted from all subsequent time point data and, since the superoxide production attained or approached plateau levels by 10 min, the resulting net values are further normalized by expressing them as percentages of their 10 min values. PMA-stimulated superoxide production is significantly more advanced at every intermediate time point in the NOXA1$_{trunc}$ transfected cells compared with NOXA1 (FIG. 4, left panel). Non-linear regression analysis carried out on each individual data set showed that the best fits are obtained using a 4-parameter sigmoid curve model, with all $R^2>0.95$ (SigmaPlot 8.0, SPSS Inc, Chicago, Ill.). Coefficients derived from the fitted curves were compared using two-tailed t-tests with unequal variance. Only the coefficient $x^0$, the time at which 50% activity was reached and therefore a measure of the displacement of the curves, was significantly different between NOXA1 and NOXA1$_{trunc}$ (5.00 min vs. 2.71 min, respectively; p<0.002). This indicated that the truncated version of NOXA1 induced PMA-stimulated activation of the NOX1 system at a significantly faster rate than the wild-type protein.

To determine whether the more rapid induction of oxidase activity with NOXA1$_{trunc}$ is due to the truncation of the C-terminal end of the molecule rather than the two Ala/Thr mutations present in the N-terminal sequence, cDNA encoding a chimeric protein is prepared (NOXA1$_{trunc}$+wt$_{(274-476)}$ (SEQ ID NO. 1 +Ala51Th4, Thr261Ala) in which NOXA1$_{trunc}$ is fully complemented with the C-terminal sequence (residues 274-476) of wild-type NOXA1. Following transfection into K562/NOX1/NOXO1 cells, this chimera is well-expressed and demonstrated induction kinetics identical to wild-type NOXA1 as shown in FIG. 4, middle panel. Thus, the rapid induction of oxidase activity observed with NOXA1$_{trunc}$ is due to the absence of the C-terminal end of the protein and not the Ala/Thr substitutions at residues 51 and 261. To delineate further the region responsible for the altered induction kinetics, a termination codon was inserted into the wild-type NOXA1 sequence at Gly residue 394 (GGA→TGA). This produced a NOXA1 protein (NOXA1$_{1-393}$) (SEQ ID NO. 1 residues 1-393) in which the C-terminal SH3 domain is deleted, but which still contained the PB1 domain as shown in FIG. 1. Transfection into the K562/NOX1/NOXO1 cells as before showed this protein to be well expressed and active, with induction kinetics similar to the NOXA1$_{trunc}$ as shown in FIG. 4, right panel. Comparison of the regression lines of NOXA1 and NOXA1$_{(1-393)}$ showed the displacement of the curves to be significant (p<0.05, n=3). Thus, the delayed induction of superoxide generating activity seen with the wild-type NOXA1 is associated primarily with the function of the SH3 domain.

EXAMPLE 10

Figure 5A:
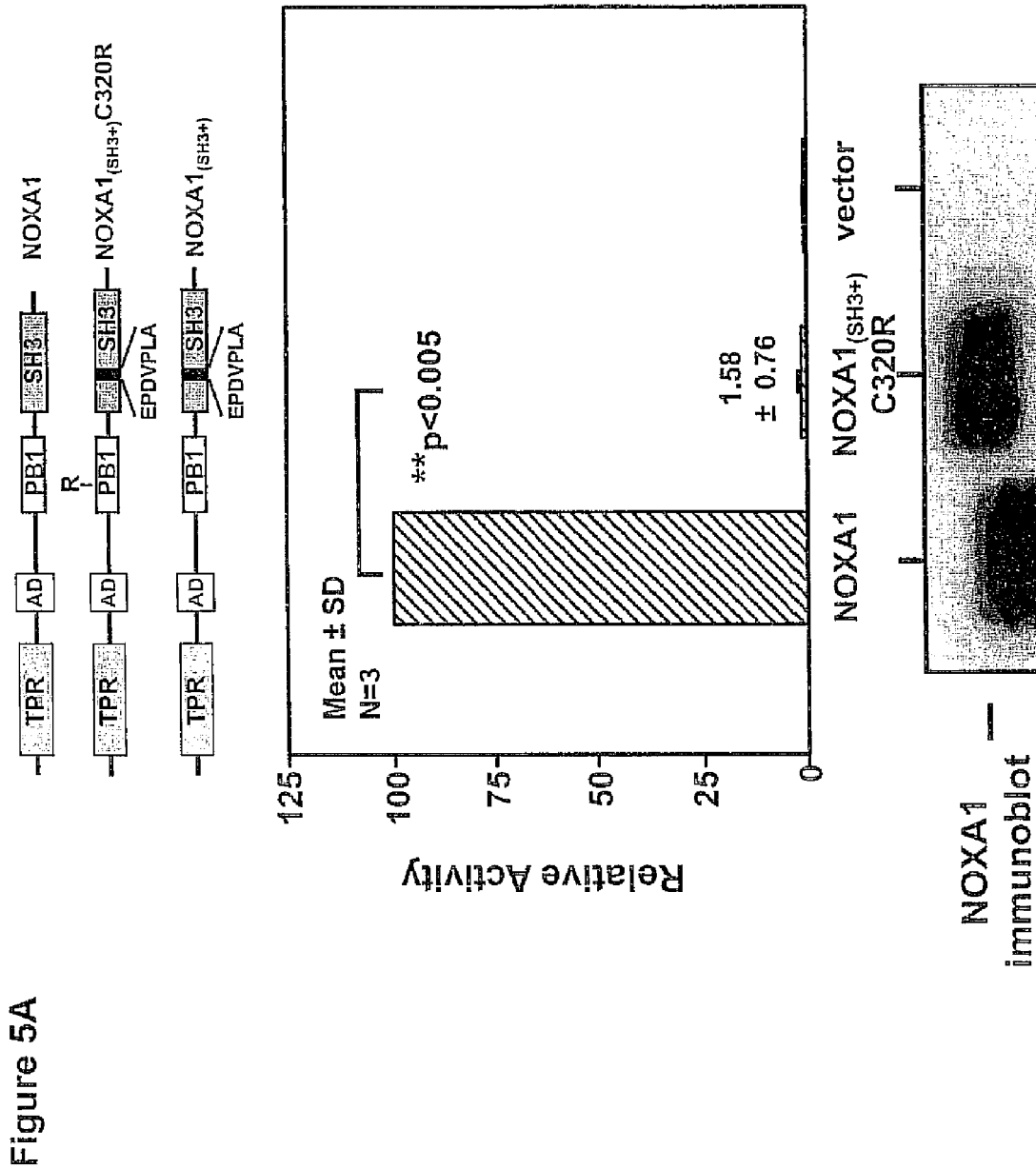
FIG. 5(A) is a relative activity plot indicating level of NOXA1 with NOXA1$_{(SH3+)}$Cys320Arg (SEQ ID NO: 3); (B) is a relative activity plot indicating level of NOXA1 (SEQ ID NO: 1) with NOXA1$_{(SH3+)}$ (SEQ ID NO: 4). The levels of the expressed NOXA1 proteins in 4×10$^5$ live transfected cells are determined by immunoblotting (see representative blot below each graph).

The Modified Form of the SH3 Domain Inhibited the Activity of NOXA1 in the Cis Configuration NOXA1$_{inhib}$ contains a heptapeptide insertion in the putative SH3 domain as shown in FIG. 1. However, the absence of exon 5 and 6 sequences in this variant also results in the deletion of residues 169-224, which include the putative activation domain of NOXA1. This variant was inactive in the K562/NOX1/NOXO1 cells. To investigate the effect of the modified SH3 domain on NOXA1 function, a chimeric molecule is first constructed by restriction digest and ligation between the cDNAs encoding the N-terminal 300 residues of NOXA1 and the complementary C-terminal end of NOXA1$_{inhib}$. This resulted in the molecule NOXA1$_{(SH3+)}$C320R, which was identical to NOXA1 except for the heptapeptide sequence $^{432}$EPDVPLA$^{438}$ (SEQ ID NO. 7) and the C320R substitution, both derived from NOXA1$_{inhib}$. When transfected into the K562/NOX1/NOXO1 cells, this construct is well expressed, but showed less than 2% (1.58±0.76; n=3) of the activity observed with wild-type NOXA1 as shown in FIG. 5A.

Figure 5B:
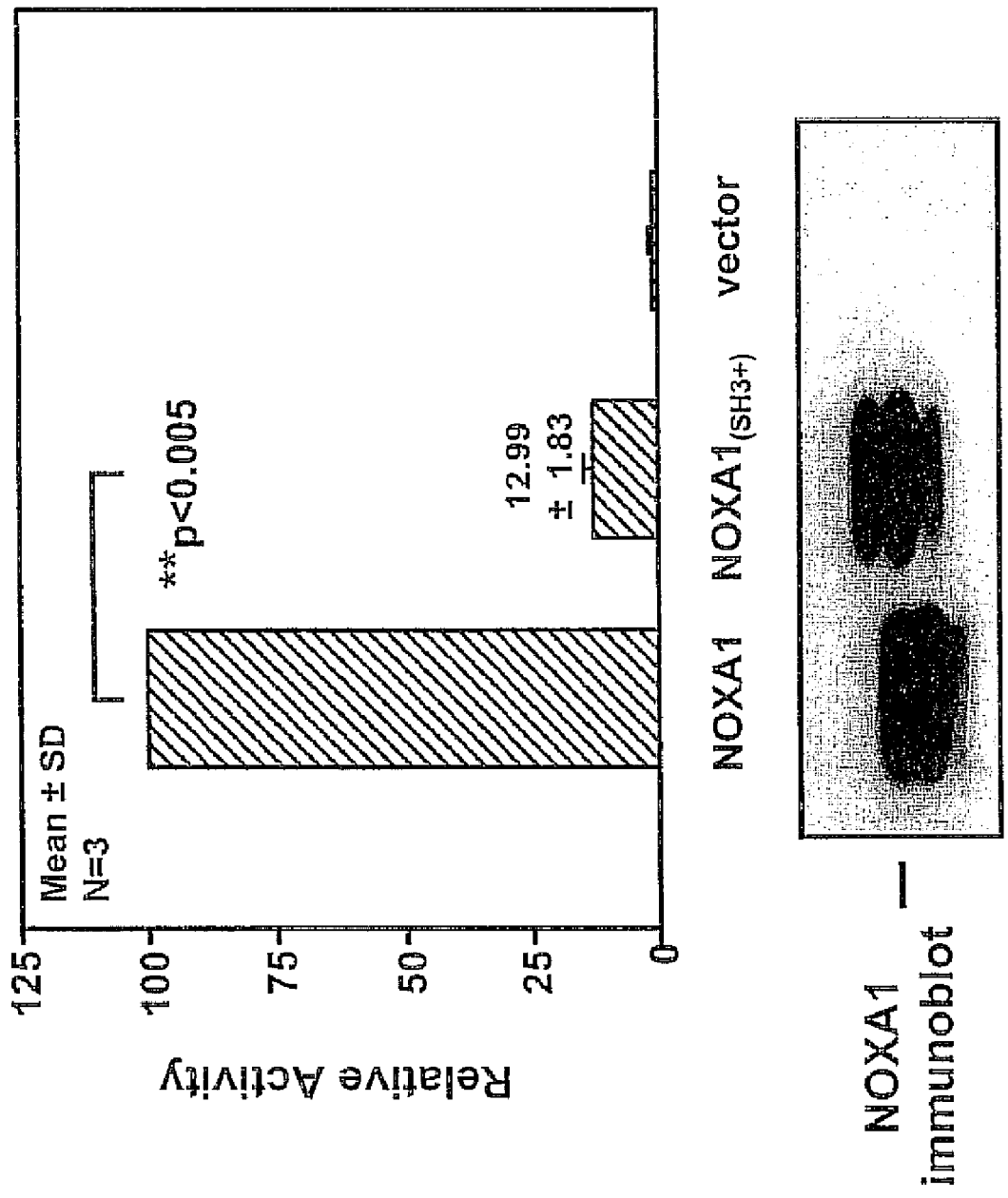

The C320R substitution is located within the PB1 domain of the molecule. The functional effect of converting the Arg residue back to the wild-type Cys residue is observed NOXA1$_{(SH3+)}$C320R→NOXA1$_{(SH3+)}$). This modified construct, identical in sequence to the NOXA1 variant deposited in the GenBank under accession # BC041594, is well expressed in the K562/NOX1/NOXO1 system as shown in FIG. 5B and, although it was somewhat more active than NOXA1$_{(SH3+)}$C320R (12.99±1.83% vs. 1.58±0.76%; n=3; p<0.016), it still demonstrated only ~10 to 15% the activity of wild-type NOXA1.

In a similar study, the cDNA for NOXA1$_{trunc}$ is complemented with the C-terminal end of NOXA1$_{inhib}$ and tested for activity as above. This construct is again well expressed in the K562/NOX1/NOXO1 cells, but showed less than 2% of the activity of NOXA1$_{trunc}$. Reinsertion of the stop codon at Gln274 restored this construct to full activity. These observations showed clearly that the insertion of the C-terminal end of NOXA1$_{inhib}$ into an otherwise active NOXA1$_{trunc}$ molecule strongly inhibited its activity. This suggests a dominant negative mechanism, rather than a loss of function. The C320R mutation appears to reinforce this inhibitory effect.

Figure 6:
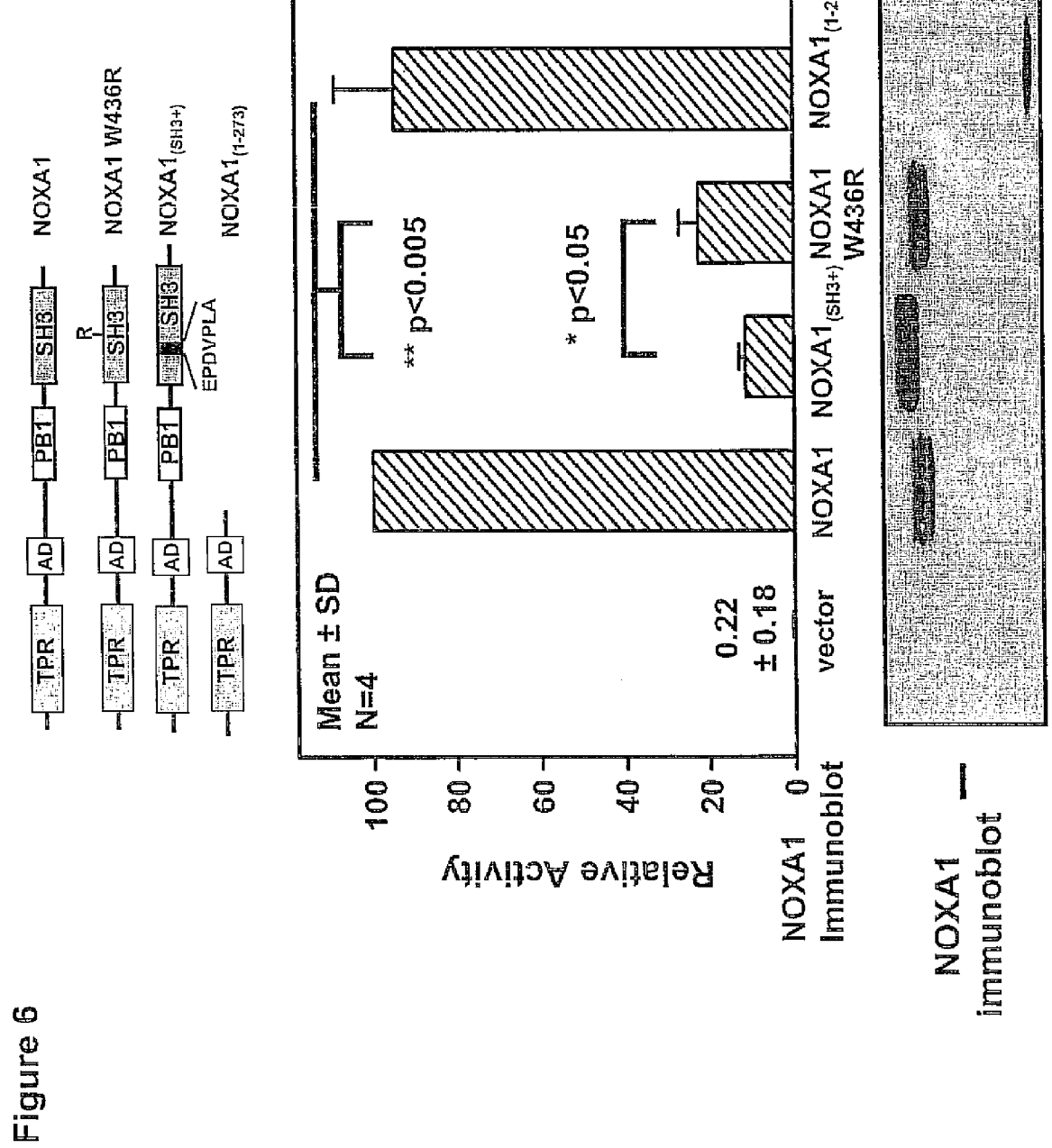
FIG. 6 is a superoxide production relative activity plot indicating level of NOXA1 variants. K562/NOX1/NOXO1 cells are transfected with the indicated plasmids NOXA1 (SEQ ID NO: 1), NOXA1$_{inhib}$ (SEQ ID NO: 2), NOXA1 W436R (SEQ ID NO: 1+Trp436Arg) and assayed for PMA-stimulated superoxide production over 10 min as in FIG. 3. Data analysis and immunoblotting are as in FIG. 5.
Figure 7:
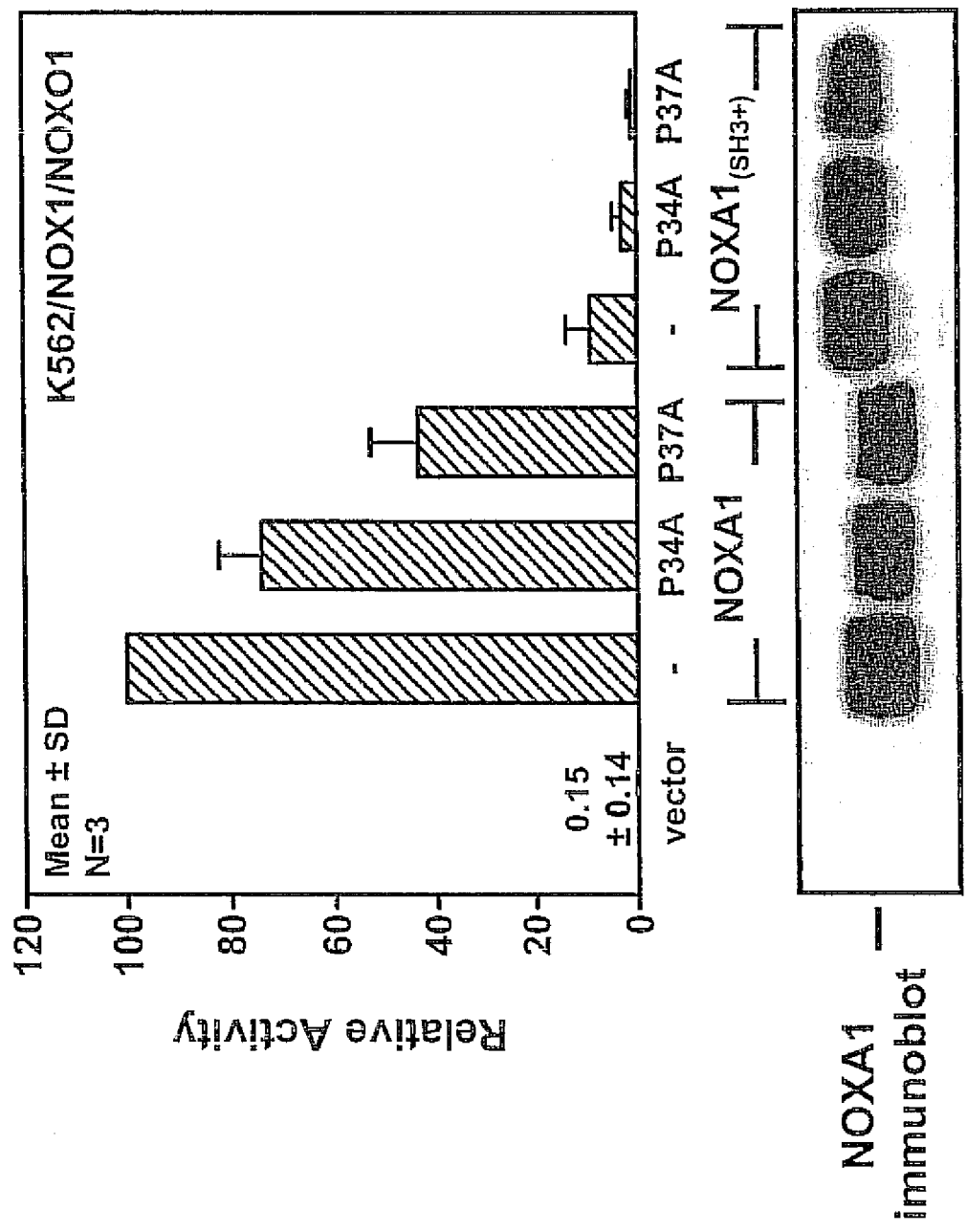
FIG. 7 is a relative activity plot showing the effect of mutation of the potential SH3 ligand-binding motif on NOXA1 (SEQ ID NO: 1), NOXA1$_{(SH3+)}$ (SEQ ID NO: 4) and NOXA1$_{trunc}$ (SEQ ID NO: 1 residues 1-273 Ala51Tyr, Tyr261Ala) function. K562/NOX1/NOXO1 cells are transfected with the indicated plasmids and assayed for PMA-stimulated superoxide production over 10 min as in FIG. 3, the effect of Pro→Ala mutations in the PxxP motif ($^{33}$VPA-PPAR$^{39}$) of wild-type NOXA1 and NOXA1$_{inhib}$ are determined by testing NOXA1 wild-type and NOXA1$_{(SH3+)}$ with separate Pro34Ala and Pro37Ala mutants with data analysis and immunoblotting as in FIG. 5.

To address this issue further, NOXA1$_{(SH3+)}$ is compared with NOXA1 in which the SH3 domain was inactivated by mutating the critical tryptophan to arginine (NOXA1W436R). In the K562/NOX1/NOXO1 transfection system, NOXA1W436R was significantly more active than NOXA1$_{(SH3+)}$ as shown in FIG. 6. Moreover, NOXA1W436R, like NOXA1$_{(SH3+)}$, is significantly less active than NOXA1(1-273) (FIG. 6), emphasizing the functional difference between inactivation of the SH3 function in the intact molecule and deletion of the PB1 and SH3 domains.

EXAMPLE 11

Figure 8:
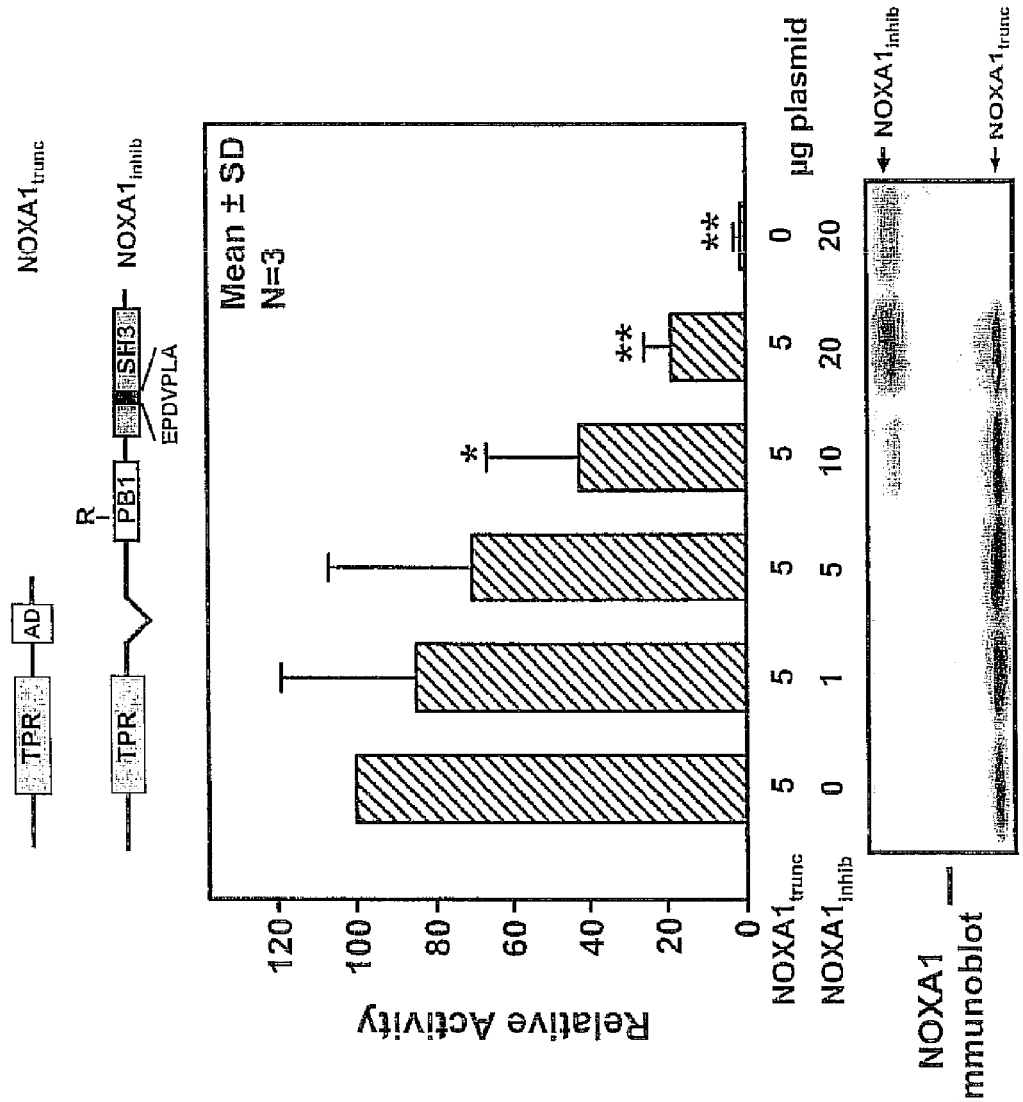
FIG. 8 is a relative activity plot showing transdominant inhibition of NOXA1$_{trunc}$ (SEQ ID NO: 1 residues 1-273 Ala51Tyr, Tyr261Ala) activity by NOXA1$_{inhib}$ (SEQ ID NO: 2). K562/NOX1/NOXO1 cells are transfected with the indicated amount of NOXA1$_{trunc}$ plasmid together with increasing amounts of the NOXA1$_{inhib}$ plasmid (per schematics above plot) in a total amount of 25 μg plasmid DNA per transfection, with the balance made up by the empty pCI-neo vector. PMA-stimulated superoxide assay, normalization of data and immunoblotting are as in FIG. 5.

NOXA1$_{inhib}$ and NOXA1$_{(SH3+)}$ Inhibited NOXA1$_{trunc}$ and NOXA1 Activity in the Trans Configuration Since both NOXA1$_{trunc}$ and NOXA1$_{inhib}$ are expressed together in the CaCo2 cells, and the modified SH3 domain of NOXA1$_{inhib}$ appears to be inhibitory for NOX1-based oxidase activity, the effect of NOXA1$_{inhib}$ co-expression on NOXA1$_{trunc}$ activity is investigated. In this experiment, a fixed amount (5 µg) of the NOXA1$_{trunc}$ expression plasmid is transfected together with increasing amounts of the NOXA1$_{inhib}$ plasmid in a total amount of 25 µg DNA, the balance being supplied with empty pCI-neo vector. NOXA1$_{inhib}$ significantly inhibited the activity of NOXA1$_{trunc}$ in a dose-dependent manner as shown in FIG. 8. This inhibition is not due to a reduction in NOXA1$_{trunc}$ expression as the corresponding immunoblots indicated similar protein levels throughout the samples. Similarly, the reduction is not due to an effect on the stably expressed NOXO1 levels, since in separate experiments it is found that this is not influenced by transient expression of NOXA1 or its variants in the K562/NOX1/NOXO1 cells.

Figure 9:
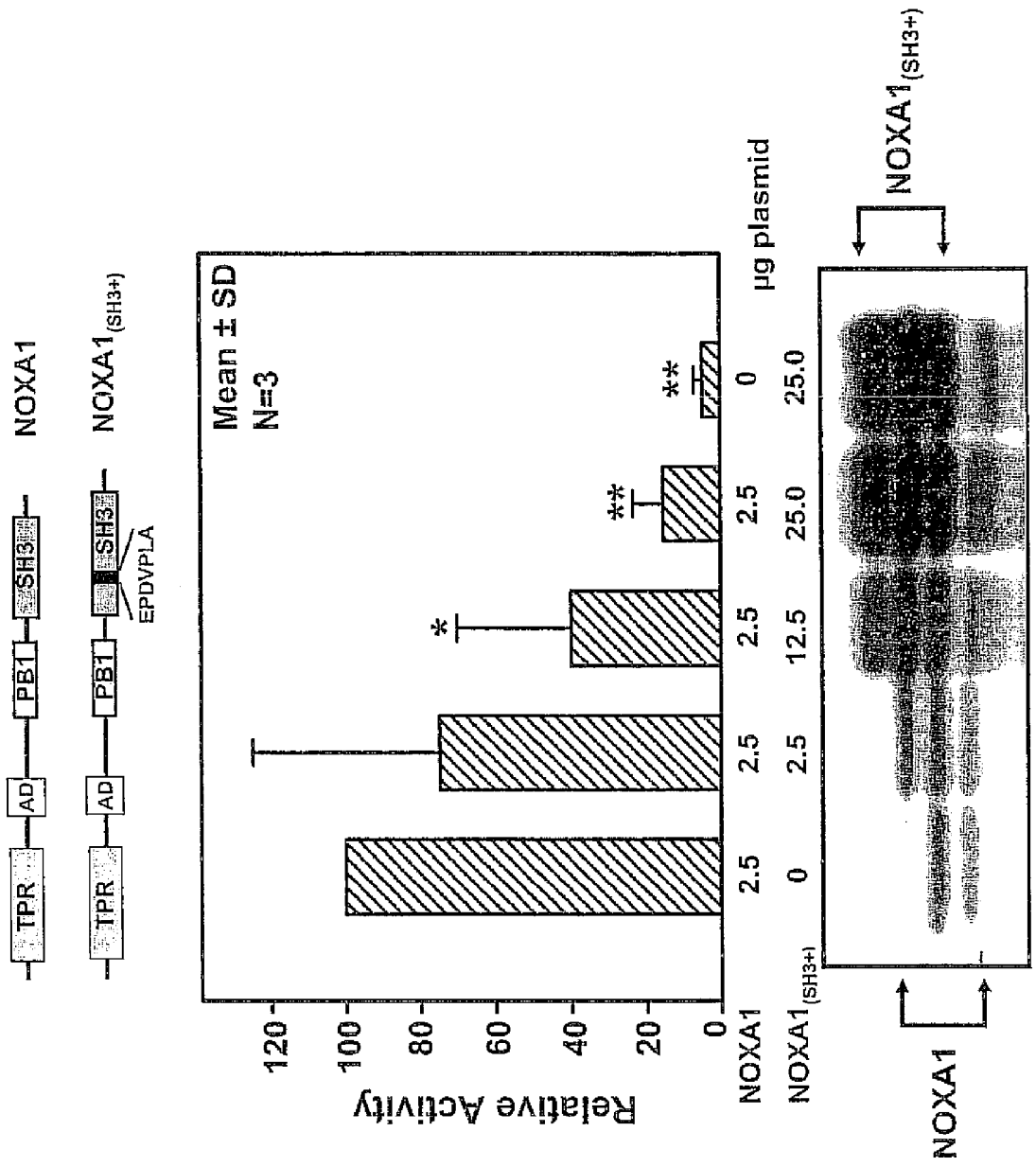
FIG. 9 is a relative activity plot showing transdominant inhibition of NOXA1 (SEQ ID NO: 1) by NOXA1$_{(SH3+)}$ (SEQ ID NO: 4). K562/NOX1/NOXO1 cells are transfected with the indicated amount of NOXA1 plasmid together with increasing amounts of the NOXA1$_{(SH3+)}$ plasmid in a total amount of 27.5 μg plasmid DNA per transfection, with the balance made up by the empty pCI-neo vector. PMA-stimulated superoxide assay, normalization of data and immunoblotting are as in FIG. 5. The means ± SD of three independent experiments are shown. In the representative NOXA1 immunoblot, the multiple band patterns of NOXA1 and NOXA1$_{(SH3+)}$ had similar mobility so that the NOXA1 bands are partially obscured by the increasing expression of NOXA1$_{(SH3+)}$. The distribution of the bands in lanes 1 and 5 is noted, which derive from the separate expression of NOXA1 and NOXA1$_{(SH3+)}$, respectively.

The ability of NOXA1$_{(SH3+)}$ to inhibit wild-type NOXA1 is studied. Because the levels of transient expression of both these molecules tended to be high, the conditions of the experiment described above are modified. A fixed amount of NOXA1 plasmid (2.5 µg DNA) is transfected with increasing amounts of NOXA1$_{(SH3+)}$ plasmid in a final amount of 27.5 µg plasmid DNA. This resulted in a significant and dose-dependent decrease in PMA-induced superoxide generating activity as shown in FIG. 9. These data indicate that NOXA1 variants containing the modified SH3 domain not only are relatively inactive, but also inhibit active NOXA1 variants in a dominant negative fashion.

EXAMPLE 12

Figure 10:
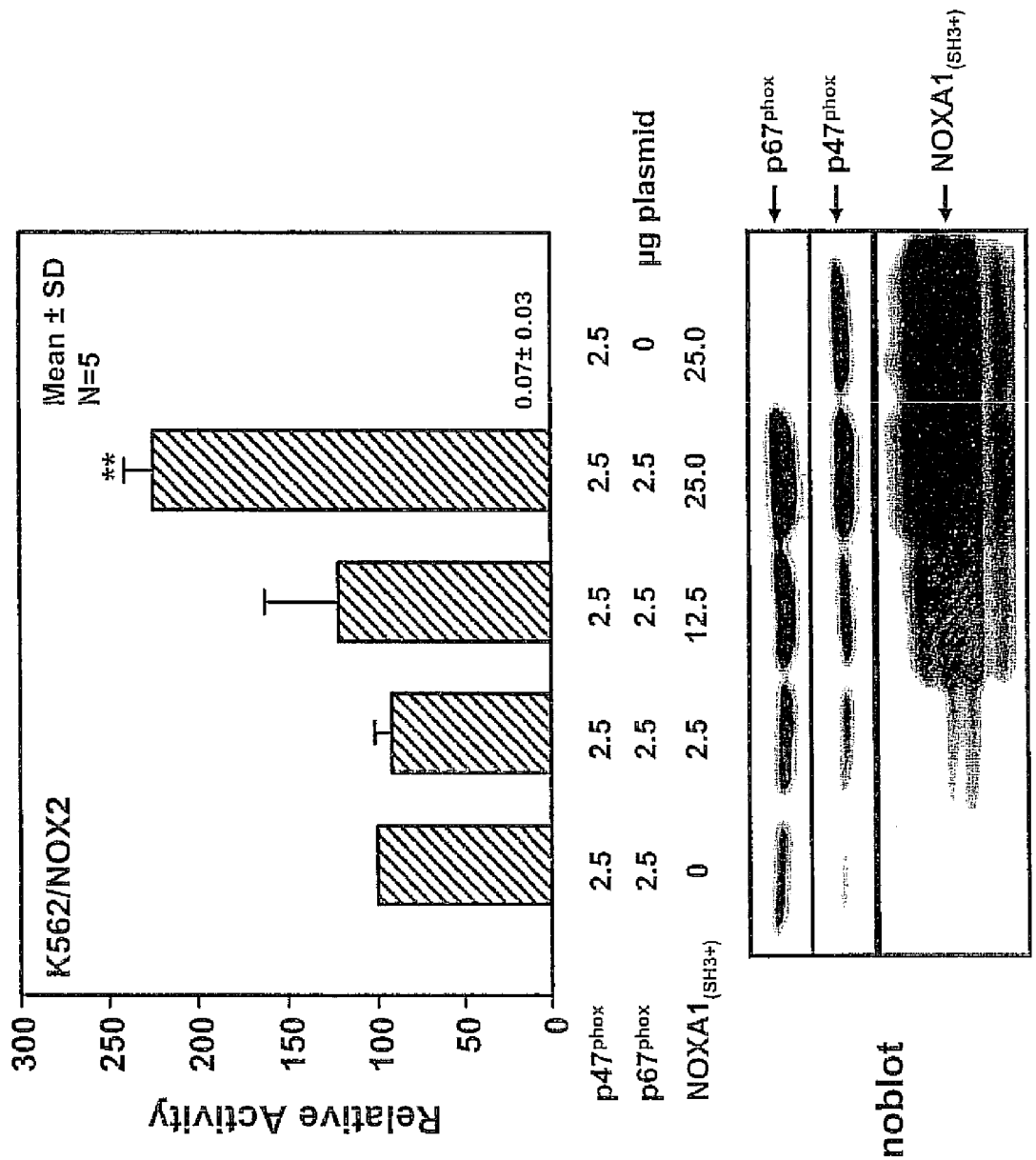
FIG. 10 is a relative activity plot showing failure of NOXA1$_{(SH3+)}$ (SEQ ID NO: 4) to inhibit superoxide generation by the NOX2/p67$^{phox}$/p47$^{phox}$ NADPH oxidase system. K562/NOX2 cells are transfected with the indicated constant amounts of human p47$^{phox}$/pcDNA3.1 and p67$^{phox}$/pCI-neo and increasing amounts of NOXA1$_{(SH3+)}$ in a total of 30 μg DNA per transfection with the balance made up by the empty pCI-neo vector. PMA-stimulated superoxide assay and normalization of data are as in FIG. 5. The means ±SD of five independent experiments are shown. Immunoblots are carried out using antibody to human NOXA1, then stripped and re-probed with antibody to p47$^{phox}$ and p67$^{phox}$.

NOXA1$_{(SH3+)}$ Does Not Inhibit the NOX2/p67$^{phox}$/p47$^{phox}$ Oxidase System in the Trans Configuration To determine if the inhibitory properties of NOXA1$_{(SH3+)}$ are specific to the NOX1/NOXA1/NOXO1 system or whether other NOX systems are also affected, co-transfection experiments are carried out in K562/NOX2 cells. K562 cells stably expressing high levels of human NOX2 (46) are transfected with equal amounts (2.5 µg each) of human p67$^{phox}$ and p47$^{phox}$ expression plasmids together with increasing amounts of either the NOXA1 or NOXA1$_{(SH3+)}$ plasmids in a total amount of 30 µg DNA. In contrast to the effect on the NOX1 system, co-expression of NOXA1$_{(SH3+)}$ showed no inhibition of the NOX2/p67$^{phox}$/p47$^{phox}$ system, despite being highly expressed in the cells (FIG. 10). In fact, there was a statistically significant increase (p<0.001, n=5) in superoxide generation in the cells transfected with the highest concentration of NOXA1$_{(SH3+)}$ plasmid. Immunoblotting with specific antibodies suggested that this increase in activity may have been due to increased expression of p67$^{phox}$ and p47$^{phox}$, perhaps resulting from stabilization of these proteins in the presence of NOXA1$_{(SH3+)}$. In similar experiments, co-transfection with wild-type NOXA1, rather than NOXA1$_{(SH3+)}$, again showed no inhibition of the NOX2 system, with only a small but insignificant increase in activity with the highest dose of the NOXA1 plasmid transfected.

These data clearly indicate that neither NOXA1 nor NOXA1$_{(SH3+)}$ inhibits the NOX-2 NADPH oxidase system in the trans configuration.

EXAMPLE 13

Binding Properties of NOXA1 and NOXA1$_{(SH3+)}$ and Their SH3 Domains

Figure 11:
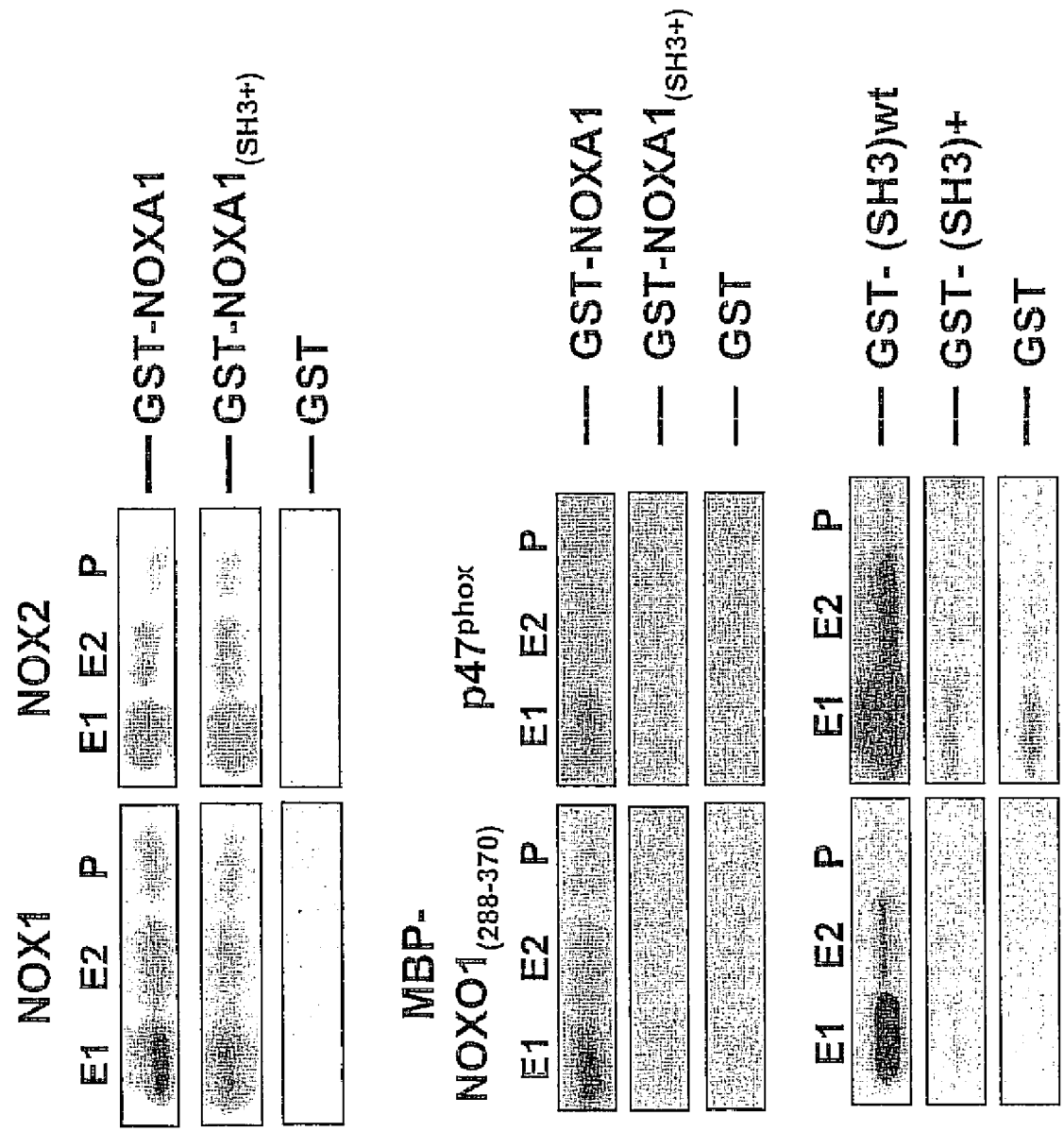
FIG. 11 is an electrophoretic separation gel depicting interaction of NOXA1 and NOXA1$_{(SH3+)}$ with other oxidase factors in vitro. $^{35}$S-labeled NOX1, NOX2, p47$^{phox}$, and MBP-NOXO1$_{(288-370)}$ are prepared by in vitro coupled transcription/ translation and the binding to immobilized GST (glutathione-S-transferase), GST-NOXA1, GST-NOXA1$_{(SH3+)}$, GST-(SH3)wt, and GST-(SH3)+. Equal volumes of the treated eluates are separated by SDS-PAGE and activity detected by fluorography. Top panels, Binding of NOX1 and NOX2 to GST-NOXA1, GST-NOXA1$_{(SH3+)}$, and GST alone. Middle panels, Binding of maltose bind protein MBP constructs MBP-NOXO1$_{(288-370)}$ and p47$^{phox}$ to GST-NOXA1, GST-NOXA1$_{(SH3+)}$, and GST alone. Bottom panels, Binding of MBP-NOXO1$_{(288-370)}$ and p47$^{phox}$ to GST and the SH3 domains of NOXA1 [GST-(SH3)wt] and NOXA1$_{(SH3+)}$ [GST-(SH3)+].

To determine if the extra peptide sequence in NOXA1$_{(SH3+)}$ modifies the protein binding properties of the molecule, in vitro GST pull-down assays are undertaken. In the first experiment, comparisons are made of NOX1 and NOX2, binding to the complete NOXA1 and NOXA1$_{(SH3+)}$ molecules fused to GST. Labeled NOX1 and NOX2, prepared by in vitro coupled transcription/translation, are mixed with the GST or GST fusion proteins bound to glutathione-Sepharose beads, and the bound activity eluted and analyzed by SDS-PAGE and fluorography. NOX1 is bound by both GST-NOXA1 and GST-NOXA1$_{(SH3+)}$ in approximately similar amounts as shown in FIG. 11, top left. No binding is seen with GST alone. This observation indicates that the inhibitory activity of NOXA1$_{(SH3+)}$ did not result from the modified SH3 domain interfering with the binding of the cofactor to the core enzyme protein, but rather to some inhibitory activity once it is bound. In identical experiments with NOX2, equivalent specific binding is again seen with both GST-NOXA1 and GST-NOXA1$_{SH3+)}$ (FIG. 11, top right). However, we have shown above that co-expression of NOXA1$_{(SH3+)}$ does not inhibit the formation of a functional NOX2/p67$^{phox}$/complex in vivo.

Using the same approach, the binding of GST-NOXA1 and GST-NOXA1$_{(SH3+)}$ to both p47$^{phox}$ and NOXO1 is also investigated. Initially, experiments are carried out using the whole NOXO1 and p47$^{phox}$ molecules. GST-NOXA1 bound the whole p47$^{phox}$ molecule specifically as shown in FIG. 11, middle panel-right. However, no binding of p47$^{phox}$ is seen with the GST-NOXA1$_{(SH3+)}$, despite the fact that the GST-NOXA1$_{(SH3+)}$ protein is relatively overloaded in these experiments. A fusion protein of maltose binding protein and the C-terminal peptide of NOXO1 (MBP-NOXO1$_{(288-370)}$), which includes the putative PxxP motif, is bound strongly and specifically by GST-NOXA1, but again, not by GST-NOXA1$_{(SH3+)}$ as shown in FIG. 11, middle panel-left. To confirm that these interactions are due to the C-terminal domains of the NOXA1 proteins that contain the SH3 domains, the experiments are repeated with fusion proteins of GST and the C-terminal NOXA1 and NOXA1$_{(SH3+)}$ polypeptides with the identical results as shown in FIG. 11, lower panels. These binding studies suggest that the loss of SH3-ligand binding activity observed with the modified NOXA1 SH3 domain may be a major contributing factor to its inactivity and inhibitory activity. Since NOXA1$_{SH3+)}$ is significantly less active than NOXA1 W436R, the loss of SH3-mediated binding to NOXO1 is by non-limiting theory believed to be not the sole mechanism for the inhibitory activity.

REFERENCES

1. Quinn, M. T. and Gauss, K. A. (2004) *J. Leukocyte Biol.* 76, 760-781.
2. Nauseef, W. M. (2004) *Histochem. Cell Biol.* 122, 277-291.
3. Groemping, Y. and Rittinger, K. (2005) *Biochem. J.* 386, 401-416.
4. Suh, Y. A., Arnold, R. S., Lassegue, B., Shi, J., Xu, X. X., Sorescu, D., Chung, A. B., Griendling, K. K., and Lambeth, J. D. (1999) *Nature* 401, 79-82.

5. Banfi, B., Maturana, A., Jaconi, S., Arnaudeau, S., Laforge, T., Sinha, B., Ligeti, E., Demaurex, N., and Krause, K.-H. (2000) *Science* 287, 138-142.
6. Geiszt, M., Kopp, J. B., Várnai, P., and Leto, T. L. (2000) *Proc. Natl. Acad. Sci. U.S.A.* 97, 8010-8014.
7. Shiose, A., Kuroda, J., Tsuruya, K., Hirai, M., Hirakata, H., Naito, S., Hattori, M., Sakaki, Y., and Sumimoto, H. (2001) *J. Biol. Chem.* 276, 1417-1423.
8. Bánfi, B., Molnár, G., Maturana, A., Steger, K., Hegedûs, B., Demaurex, N., and Krause, K. H. (2001) *J. Biol. Chem.* 276, 37594-37601.
9. Cheng, G. J., Cao, Z. H., Xu, X. X., Van Meir, E. G., and Lambeth, J. D. (2001) *Gene* 269, 131-140.
10. Yang, S., Madyastha, P., Bingel, S., Ries, W., and Key, L. (2001) *J. Biol. Chem.* 276, 5452-5458.
11. Bánfi, B., Malgrange, B., Knisz, J., Steger, K., Dubois-Dauphin, M., and Krause, K. H. (2004) *J. Biol. Chem.* 279, 46065-46072.
12. Bánfi, B., Tirone, F., Durussel, I., Knisz, J., Moskwa, P., Molnár, G. Z., Krause, K. H., and Cox, J. A. (2004) *J. Biol. Chem.* 279, 18583-18591.
13. Gorin, Y., Ricono, J. M., Kim, N. H., Bhandari, B., Choudhury, G. G., and Abboud, H. E. (2003) *Am. J. Physiol. Renal Physiol.* 285, F219-F229.
14. Mahadev, K., Motoshima, H., Wu, X. D., Ruddy, J. M., Arnold, R. S., Cheng, G. J., Lambeth, J. D., and Goldstein, B. J. (2004) *Mol. Cell. Biol.* 24, 1844-1854.
15. Pedruzzi, E., Guichard, C., Olivier, V., Driss, F., Fay, M., Prunet, C., Marie, J. C., Pouzet, C., Samadi, M., Elbim, C., O'Dowd, Y., Bens, M., Vandewalle, A., Gougerot-Pocidalo, M. A., Lizard, G., and Ogier-Denis, E. (2004) *Mol. Cell Biol.* 24, 10703-10717.
16. Paffenholz, R., Bergstrom, R. A., Pasutto, F., Wabnitz, P., Munroe, R. J., Jagla, W., Heinzmann, U., Marquardt, A., Bareiss, A., Laufs, I., Russ, A., Stumm, G., Schimenti, J. C., and Bergstrom, D. E. (2004) *Genes Dev.* 18, 486-491.
17. Cheng, G. J., Ritsick, D., and Lambeth, J. D. (2004) *J. Biol. Chem.* 279, 34250-34255.
18. Bánfi, B., Clark, R. A., Steger, K., and Krause, K. H. (2003) *J. Biol. Chem.* 278, 3510-3513.
19. Takeya, R., Ueno, N., Kami, K., Taura, M., Kohjima, M., Izaki, T., Nunoi, H., and Sumimoto, H. (2003) *J. Biol. Chem.* 278, 25234-25246.
20. Geiszt, M., Lekstrom, K., Witta, J., and Leto, T. L. (2003) *J. Biol. Chem.* 278, 20006-20012.
21. *Proteins-Structure and Molecular Properties*, 2nd Ed., T. E. Creighton, W. H. Freeman and Company, New York (1993). [page cite needed]
22. *Posttranslational Covalent Modification of Proteins*, B. C. Johnson, Ed., Academic Press, New York, pgs. 1-12 (1983).
23. Seifter, S. and Englard, S. (1990) *Meth. Enzymol.* 182, 626-646 (1990).
24. Rattan, S. I., Derventzi, A., and Clark, B. F. (1992) *Ann. N.Y. Acad. Sci.* 663, 48-62.
25. Brugge, J. S., Cotton, P. C., Queral, A. E., Barrett, J. N., Nonner, D., and Keane, R. W. (1985) *Nature* 316, 554-557.
26. Gitlin, L., Karelsky, S., and Andino, R. (2002) *Nature* 418(6896), 430-4.
27. Semizarov, D., Frost, L., Sarthy, A., and Kroeger, P. (2004) *Nucleic Acids Res.* 32(13), 3836-3845.
28. Brummelkamp, T. R., Bernards, R., and Agami, R. (2002) *Cancer Cell* 2(3), 243-7.
29. U.S. Pat. No. 6,774,120.

L.VII.5. Role of Homologous Recombination in Providing Chromosomal Stability and Protection Against DNA Crosslinks in Mammalian Cells Godthelp B. C.[1], Wiegant W. W.[1], van Buul P. P. W.[1], Joenje H.[2], Arwert F.[2], Kanaar R.[3], and Zdzienicka M. Z.[1,4]

[1] Dept of Radiation Genetics and Chemical Mutagenesis, Leiden University Medical Center, Leiden, The Netherlands
[2] Dept of Clinical Genetics and Human Genetics, Free University Medical Center, Amsterdam, The Netherlands
[3] Dept of Cell Biology and Genetics, Erasmus University, Rotterdam, The Netherlands
[4] Dept of Molecular Cell Genetics, The Ludwik Rydygier University of Medical Sciences, Bydgoszcz, Poland.

Homologous recombination (HR) plays an essential role in the maintenance of genome integrity and in the cellular response to DNA damage. Recently, compelling evidence suggest that HR also plays a role in processing DNA interstrand cross-links (ICLs) that are introduced by commonly used anti-cancer drugs such as cisplatin or mitomycin C, The existence of multiple complementation groups in MMC-sensitive human disorders and rodent cell mutants indicates complexity of the mechanisms involved. Rad51 plays a key role in HR and displays a highly dynamic distribution in nuclear foci following DNA damage. Rad51 interacts with many proteins, including the proteins encoded by the breast cancer susceptibility genes, BRCA1 and BRCA2. Following DNA damage, Rad51 forms nuclear foci in which Xrcc2, Xrcc3, Rad51B, Rad51C, Rad51D, Rad52 and Rad54 are also involved. Recently, we identified two MMC-sensitive hamster cell mutants that are impaired in Rad51 foci formation in response to DNA damage. We found that one is defective in Brca2 and the other in Rad51C. The phenotype of these mutants indicates that both proteins function in DNA-cross-link resistance and genomic stability, however Rad51C is also involved in sister chromatid cohesion. Like the MMC-sensitive hamster cell mutants, cells derived from Fanconi anemia (FA) patients are characterized by chromosomal instability and a specific hypersensitivity to ICLs. Therefore, we also examined Rad51 foci formation in response to DNA damage in all complementation groups of FA. Clearly, only fibroblasts derived from FA complementation group D1 are impaired in this process. FA is an autosomal recessive disorder characterized by progressive bone marrow failure, various congenital malformations and marked predisposition to malignancies. Despite cloning of six FA genes, this pathway remains mysterious. Thus, our observations imply, that unlike all other FA proteins known to date, the product of the FANCD1 gene is involved in the assembly and/or stabilization of the Rad51 protein complex, suggesting that FANCD1 is likely to be involved in HR-dependent ICL repair. Our results underline the role of HR in the protection of mammalian cells against ICLs and in maintaining chromosome integrity by controlling several different processes, such as mutagenesis, cell cycle progression, centrosomes and sister chromatid cohesion.

I.P.7. The Effect of *E. coil* recA Expression on the Sensitivity of *S. cerevisiae* rad51 and rad52 Mutants to DNA Damaging Agents Dudáš A.[1], Marková E.[1], Chovanec M.[1], Vlasáková D.[1], Vlčková V.[2], Lampartová Z.[2], and Brozmanová J.[1]

[1] Cancer Research Institute SAS, Bratislava, Slovak Republic
[2] Dept. of Genetics, Faculty of Natural Sciences, Comenius University, Slovak Republic DNA double-strand breaks (DSBs) are perhaps the most deleterious DNA lesions as they disrupt both DNA strands causing problems for all DNA transactions. If left unrepaired, they can cause chromosomal fragmentation, translocations and deletions, a consequence of which might be cell death, or in multicellular organism, cancer. DSBs are generated by a wide range of factors, including ionizing radiation (IR), free radicals—the products of oxidative metabolism and radiomimetic chemicals such as methyl methanesulfonate (MMS).

The RecA protein plays a pivotal role in homologous recombination (HR) in *E.coli*. In *S. cerevisiae*, the RAD52 epistasis group of genes is thought to represent a pathway for DSB repair by HR. Two genes of the group, RAD51 and RAD52, were shown to have key roles in this process. The product of the RAD51 gene has been found to have extensive structural homology with the *E. coli* RecA protein. On the other hand, the RAD52 encoded product does not show obvious homology to any known recombination proteins in bacteria and therefore appears to be unique to eukaryotes. The importance of the RAD52 gene is underlined by the presence of homologues in all eukaryotic organisms investigated to date.

We have tested effect of the *E. coli* recA expression on the sensitivity of the *S. cerevisiae* rad51 and rad52 mutants to the agents creating the DNA DSBs such as MMS, IR and hydrogen peroxide ($H_2O_2$). We have found that the RecA protein increases survival of the rad52 mutants to IR, MMS and $H_2O_2$. On the other hand, no effect of recA expression on sensitivity to these agents was observed in the rad51 mutant Survival data are in good correlation with the increased efficiency to repair DSBs, as measured by pulsed field gel electrophoresis, in the rad52 and rad51 strains expressing RecA. Thus, it seems that the RecA protein can participate in DSB repair in yeast unless the Rad51 protein is present. As DSBs repair in yeast is mediated by the multiprotein complex, the two hybrid experiments are in progress in our laboratory to verify possible involvement of RecA in protein-protein interactions within this complex.

I.P.10. Long-Chain Adducts of trans-4-hydroxy-2-nonenal to DNA Bases Cause Mainly Recombination and Frameshift Mutations Kowalczyk P., Cieśla J. M., Kuśmierek J. T., and Tudek B.

Institute or Biochemistry and Biophysics PAS, Warsaw, Poland

One of the most abundant products of lipid peroxidation is trans-4-hydroxy-2-nonenal (HNE), with concentration in human plasma ranging between 0.1-1 µM. We have previously shown that HNE produces adducts to all four DNA bases (poster I.P.12), which are characterised by the presence of long 6-7 carbon atom chains in addition to exocyclic etheno-rings and possibly propano-. DNA polymerase fingerprinting on HNE-modified templates suggests that the presence of these adducts in DNA stops replication by T7 DNA polymerase, and that reactivity of DNA bases with HNE follows the order: dG>dC>dA≧dT.

Mutagenicity studies in M13 phage system shows that modification of phage DNA with HNE decreases phage survival in JM105 strain and increases mutation frequency in M13 lacZ gene in a time and dose dependent manner. As much as 40-fold increase in mutation frequency (at 8% survival) was observed after 2 h of DNA modification with 2 mM HNE at pH 5.5. Sequence analysis of M13 lacZ mutants revealed that the most frequent mutations were recombination events with the lacZ gene of F' factor, detected as simultaneous deletion of 93 (ΔM15 deletion of F'lacZ) and 54 (M13 polylinker) nucleotide fragments of phage DNA. Similar numbers of base substitutions and frameshift mutations were found. The major base substitution was C→T transition. This mutation constituted 37% of all point mutations. Interestingly, 37% of point mutations were frameshifts, and this was 4-fold higher level than that observed in the spectrum of spontaneous mutations. Within frameshifts one nucleotide additions of cytidine and guanosine prevailed and to a lesser extent deletions, mainly A deletions, were found. Additions/deletions were found almost exclusively in runs of C, G or A. Thus, template damage probably evoked DNA polymerase "jump" over the lesion, during which the enzyme added one nucleotide to reach the template behind HNE adduct with a long side-chain. Such mechanism could also explain a high number of recombinations, where DNA polymerase could switch to undamaged homologous template of F' factor.

I.PO.37. Ubiquitination Determines Balance Between Homologous Recombination (HR) and Endjoining (NHEJ) in YEAST Mörtl S., Ahne F., Kistler M., and Eckardt-Schupp F.

GSF-Institute of Molecular Radiobiology, Neuherberg, Germany.

The Ubiquitin Proteasome Pathway is required for the regulation of various cellular processes. It has been proven for *Saccharomyces cerevisiae* that postreplication repair is also assigned to ubiquitination (1). The RAD6, UBC13, MMS2 genes encode ubiquitin-conjugating enzymes (E2), and the RAD18 and RAD5 genes code for RING finger proteins which function as ubiqitin ligases (E3) and mediate physical contacts between the members of the RAD6 pathway. Rad5p recruits the Ubc13p-Mms2p complex, and Rad5p association with Rad18p brings it into contact with the Rad6p/Rad18p complex. The Rad6p/Rad18p complex and the Rad5p/Ubc13/Mms2 complex differ in the type of ubiquitination. Rad5p has a regulatory function for the repair of restriction enzyme-mediated deletions in plasmids. In RAD5-proficient cells, correct DSB and gap repair of plasmids occur by (HR) only. In rad5 mutants, 75% of gap repair is performed by NHEJ (2).

In order to study the roles of the RAD6 group proteins for the regulated HR/NHEJ balance, we analysed rad6, rad18, ubc13, mms2 mutants and the respective rad5 double mutants using a two-marker plasmid. ubc13, mms2 and the double mutants show 30% correct repair by HR while the remaining 70% were repaired by NHEJ yielding ura-clones. rad6 and rad18 mutants, however, restore the gap by HR nearly as efficient as wildtype. In rad5/18 and rad5/6 double mutants, the rad5 phenotype is fully suppressed which supports the biochemical findings that Rad5p, Rad6p and Rad18p act in a complex (1). We propose that the regulatory decision whether gap repair of plasmid DNA is performed by HR or NHEJ depends on the Lys48- or Lys63-type of ubiquitination controlled by the different members of the RAD6 epistasis group. These differences in ubiquitination may have differential impact on the degradation or conformational changes of chromatin proteins. Chromatin conformation in turn may determine whether gap repair of the plasmid DNA is done by HR. As E2 and E3 homologues of the RAD6 group exist in mammalian cells we speculate that their specific HR/NHEJ balance may be as well dependent on differential ubiquitination.

I.PO.40. Studies on Mechanisms Involved in Mammalian Mutagenesis

Johanason F.[1], Ayouaz A.[1], Jenssen D.[1], Erixon K.[1], Lundin C.[1], Schultz N.[1], and Helleday T.[1,2].

[1] Dept. of Genetic and Cellular Toxicology, Stockholm University, Sweden
[2] The Institute for Cancer Studies, University of Sheffield, United Kingdom By applying new methodology, we have challenged the interplay between the processes involved in bypass mechanisms during replication stress and their importance for establishing gene mutations. When DNA replication is stalled due to non-coding DNA lesions, mechanisms are triggered that can bypass the lesions during replication. During the bypass process, the so-called translesion synthesis (TLS), double strand breaks (DSB) may be formed, which trigger repair by homologous recombination (HR) or non-homologous end-joining (NHEJ). We used the alkaline DNA unwinding technique (Ahnström and Erixon, 1981) to study replication gaps from different lesions and at the same time, investigated the level of mutations induced in the hprt gene (Jenssen, 1984). In parallel, we apply studies on homologous recombination by using the SPD8 cell line, which is a mutant exhibiting a partial tandem copy of the hprt gene found to revert by a rad51-supported homologous recombination mechanism (Arnaudeau et al., 1999). We found earlier a good correlation between the level of replication gaps per loci and the number of mutations induced in the hprt gene (Jenssen at al, 2002). The results indicated that the level of mutations induced by alkylating agents was in agreement with expectation of the low fidelity DNA polymerases, e.g., about 1 per $10_4$. Furthermore, our recent findings were that when recombination pathways are blocked, increased levels of mutations were obtained. We suggest, as a working hypothesis, that TLS might be interplay between pathways involving low fidelity DNA polymerases and recombination mechanisms, the former pathway being more error-prone. Thus, the level of mutations formed might be a mailer of competition between the type of substrate formed during replication stress and the proteins involved in different alternative bypass mechanisms.

I.P.60 Role of Mismatch Repair in the Processing of DNA Damage Induced by CCNU

Russo M. T., Aquilina C., Sapora O., Crescenzi M., and Bignami M.

Istituto Suporiore di Sanita', Roma, Italy.

Mismatch repair (MMR)-deficient cells can be hypersensitive, both in vitro and in vitro, to killing induced by chemotherapeutic agents that introduce interstrand DNA crosslinks (ICLs). These drugs include cyclohexylchloroethylnitrosourea (CCNU) and mitomycin C. Recent data indicate that double strand breaks (DSBs) are formed as intermediates during the repair of ICLs. Several proteins (XRCC1, XRCC2, XPA and XPF), which are known to have a role in nucleotide excision repair (NER) or in homologous recombination, have been proposed to be involved in the repair of ICLs. We have investigated whether MMR plays a role in the processing of DSBs induced by CCNU. As a model system we used the MMR-proficient Raji cells, derived from a Burkitt lymphoma, and an hMLH1-defective derivative Clone R10. DSBs, as monitored by Field Inversion Gel Electrophoresis (FIGE), appeared 3-6 hr after exposure to CCNU. No significant difference in DSBs formation was observed in the two cell lines suggesting that loss of MMR does not affect the initial steps of ICLs repair. Twelve hours after 1 hr exposure to CCNU MMR-proficient and -deficient cells showed a similar delay in the progression through the S phase of the cell cycle, as determined by cytofluorimetric analyses. Exposure to CCNU induced, however, increased levels of apoptosis in the MMR-defective variant compared to the MMR-proficient Raji cells. The critical event in this differential induction of apoptosis resulted to be the transition through the S phase of the cell cycle. Inhibition of S phase progression by the use of aphidicolin abolished the MMR-dependent apoptosis induced by CCNU. By using this experimental approach we were also able to show that MMR-deficient cells display slow kinetics in the rejoining of these DSBs. Immunofluorescence experiments with specific antibodies against the MRE11 and RAD51 proteins identified alterations in the kinetics of nuclear foci localization at sites of recombination associated with loss of MMR. These data strongly suggest that MMR is required for the correct processing of DNA damage induced by CCNU.

31. U.S. Pat. No. 4,980,286.
32. Wu, G. Y., and Wu, C. H. (1987) *J. Biol. Chem.* 262, 4429-4432.
33. WO 92/06180, WO 92/22635, WO 92/20316, WO 93/14188, WO 93/20221.
34. Perales, J. C., Ferkol, T., Beegen, H., Ratnoff, O. D., and Hanson, R. W. (1994) *PNAS* 91(9), 4086-4090.
35. Midoux, P., Mendes, C., Legrand, A., Raimond, J., Mayer, R., Monsigny, M., and Roche, A. C. (1993) *Nucleic Acids Res.* 21(4), 871-878.
36. Yakubov, L. A., Deeva, E. A., Zarytova, V. F., Ivanova, E. M., Ryte, A. S., Yurchenko, L. V., and Vlassov, V. V. (1989) *PNAS* 86(17), 6454-6458.
37. Ferkol, T., Perales, J. C., Mularo, F. and Hanson, R. W. (1996) *PNAS* 93(1), 101-105.
38. Luo, D. and Saltzman, W. M. (2002) *Nat. Biotechnol.* 18(1), 33-37.
39. Peitz M., Pfannkuche K., Rajewsky K., and Edenhofer F. (2004) *Proc. Natl. Acad. Sci. U.S.A.* 99:4489-4494.
40. Jo D., Nashabi A., Doxee C., Lin Q., Unutmaz D., Chen J., and Ruley H. E. (2001) *Nat. Biotechnol.* 19:929-933.
41. McLean, J. W., Fox, E. A., Baluk, P., Bolton, P. B., Haskell, A., Pearlman, R., Thurston, G., Umemeto, E. Y., and McDonald, D. M. (1997) *Am. J. Physiol. Heart Circ. Physiol.* 273 (1 Pt. 2), H387-404.
42. Remington: The Science and Practice of Pharmacy, (2000) pp 858-892.
43. Sachdev, D. and Chirgwin, J. M. (1998) *Protein Expression & Purification* 12, 122-132.
44. Strausberg, R. L., Feingold, E. A., Grouse, L. H., Derge, S. G., Klausner, R. D., Collins, F. S., Wagner, L., Shenmen, C. M., Schuler, G. D., Altschul, S. F., Zeeberg, B., Buetow, K. H., Schaefer, C. F., Bhat, N. K., Hopkins, R. F., Jordan, H., Moore, T., Max, S. I., Wang, J., Hsieh, F., Diatchenko, L., Marusina, K., Farmer, A. A., Rubin, G. M., Hong, L., Stapleton, M., Soares, M. B., Bonaldo, M. F., Casavant, T. L., Scheetz, T. E., Brownstein, M. J., Usdin, T. B., Toshiyuki, S., Carninci, P., Prange, C., Raha, S. S., Loquellano, N. A., Peters, G. J., Abramson, R. D., Mullahy, S. J., Bosak, S. A., McEwan, P. J., McKernan, K. J., Malek, J. A., Gunaratne, P. H., Richards, S., Worley, K. C., Hale, S., Garcia, A. M., Gay, L. J., Hulyk, S. W., Villalon, D. K., Muzny, D. M., Sodergren, E. J., Lu, X., Gibbs, R. A., Fahey, J., Helton, E., Ketteman, M., Madan, A., Rodrigues, S., Sanchez, A., Whiting, M., Madan, A., Young, A. C., Shevchenko, Y., Bouffard, G. G., Blakesley, R. W., Touchman, J. W., Green, E. D., Dickson, M. C., Rodriguez, A. C., Grimwood, J., Schmutz, J., Myers, R. M., Butterfield, Y. S., Krzywinski, M. I., Skalska, U., Smailus, D. E., Schnerch, A., Schein, J. E., Jones, S. J., and Marra, M. A. (2002) *Proc. Natl. Acad. Sci. U.S.A.* 99, 16899-16903.
45. Kami, K., Takeya, R., Sumimoto, H., and Kohda, D. (2002) *EMBO J.* 21, 4268-4276.
46. Clark, R. A. and Valente, A. J. (2004) *Mech. Ageing Dev.* 125, 799-810.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A purified recombinantly expressed polypeptide comprising an NADPH oxidase cytosolic cofactor p67$^{phox}$ having a C-terminal SH3 domain insertion mutation of at least 3 consecutive amino acids positioned between Pro-Glu-Asp-Leu (SEQ ID NO: 35) and Gly-Ile-Phe-Pro-Lys (SEQ ID NO: 34) motifs of said SH3 domain so as to reduce activity of said cofactor relative to a wild-type cofactor of SEQ ID NO: 5 for a p67$^{phox}$ mutant, wherein said insertion mutation has a net hydropathic index of between −2.4 and 1.6; and an excision, addition or deletion mutation within bases 199-213, which is an activation domain of said cofactor to further reduce activity of said cofactor.

2. A purified recombinantly expressed polypeptide comprising an NADPH oxidase cytosolic cofactor p67$^{phox}$ having a C-terminal SH3 domain insertion mutation of at least 3 consecutive amino acids positioned between Pro-Glu-Asp-Leu (SEQ ID NO: 35) and Gly-Ile-Phe-Pro-Lys (SEQ ID NO: 34) motifs of said SH3 domain so as to reduce activity of said cofactor relative to a wild-type cofactor of SEQ ID NO: 5 for a p67$^{phox}$ mutant wherein said insertion mutation has a net hydropathic index of between −2.4 and 1.6; and a point mutation from tryptophan at residue 494 of said p67$^{phox}$ cofactor.

3. The polypeptide of claim 2 wherein said point mutation is to an arginine residue.

4. A purified recombinantly expressed polypeptide comprising an NADPH oxidase cytosolic cofactor NOXA1 (SEQ ID NO: 1) having an SH3 C-terminal domain insertion mutation of at least 3 consecutive amino acids inserted between Pro-Glu-Asp-Leu (SEQ ID NO: 35) and Gly-Ile-Phe-Pro-Lys (SEQ ID NO: 34) motifs of said SH3 C-terminal domain and at least one additional mutation selected from the group consisting of: an excision, addition or deletion mutation within bases 200-214 of an activation domain of said cofactor to further reduce activity of said cofactor, a point mutation changing a tryptophan at residue 436 of said NOXA1 cofactor, and a nonsilent mutation within a PB1 domain so as to reduce activity of said cofactor relative to a wild-type cofactor of SEQ ID NO: 1 for said NOXA1 cofactor, wherein said insertion mutation has a net hydropathic index of between −2.4 and 1.6.

5. A pharmaceutical composition comprising: a polypeptide according to claim 4 and a pharmaceutically acceptable carrier.

6. pharmaceutical composition of claim 5 wherein said polypeptide further comprises a transmembrane transporter polypeptide covalently bonded thereto.

7. The pharmaceutical composition of claim 5 further comprising an encapsulant for the polypeptide selected from the group consisting of: a liposome, microparticles, and microcapsules.

8. The pharmaceutical composition of claim 5 wherein said peptide is present in the form of a pharmaceutically acceptable salt.

9. The polypeptide of claim 1 wherein said mutation within bases 199-213 is deletion of bases 199-213.

10. The polypeptide of claim 4 wherein said point mutation is to an arginine residue.

11. The polypeptide of claim 4 wherein said mutation within bases 200-214 is deletion of bases 200-214.

* * * * *

UNITED STATES PATENT AND TRADEMARK OFFICE
CERTIFICATE OF CORRECTION

| | | |
|---|---|---|
| PATENT NO. | : 7,582,606 B2 | Page 1 of 1 |
| APPLICATION NO. | : 11/556314 | |
| DATED | : September 1, 2009 | |
| INVENTOR(S) | : Anthony J. Valente et al. | |

It is certified that error appears in the above-identified patent and that said Letters Patent is hereby corrected as shown below:

Col. 1, before line 5 insert:

--This invention was made with government support under grant numbers AI020866 and AI019519 awarded by the National Institutes of Health. The government has certain rights in the invention.--

Signed and Sealed this

Thirtieth Day of March, 2010

David J. Kappos
*Director of the United States Patent and Trademark Office*